US008911498B2

(12) United States Patent
Bartish, Jr. et al.

(10) Patent No.: US 8,911,498 B2
(45) Date of Patent: Dec. 16, 2014

(54) INTERVERTEBRAL PROSTHETIC DISC

(75) Inventors: Charles M. Bartish, Jr., Providence, RI (US); Katherine Torres, North Dartmouth, MA (US); J. Riley Hawkins, Cumberland, RI (US); S. Daniel Kwak, Grafton, MA (US)

(73) Assignee: DePuy Synthes Products, LLC, Raynham, MA (US)

( * ) Notice: Subject to any disclaimer, the term of this patent is extended or adjusted under 35 U.S.C. 154(b) by 1789 days.

(21) Appl. No.: 11/055,025

(22) Filed: Feb. 10, 2005

(65) Prior Publication Data

US 2006/0178745 A1     Aug. 10, 2006

(51) Int. Cl.
*A61F 2/44* (2006.01)
*A61F 2/28* (2006.01)
*A61F 2/30* (2006.01)

(52) U.S. Cl.
CPC ............. *A61F 2/4425* (2013.01); *A61F 2/442* (2013.01); *A61F 2002/2817* (2013.01); *A61F*
(Continued)

(58) Field of Classification Search
CPC ..... A61F 2/442; A61F 2/4455; A61F 2/4611; A61F 2002/448; A61B 17/70
USPC ............................................ 623/17.11–17.16
See application file for complete search history.

(56) References Cited

U.S. PATENT DOCUMENTS 3,867,728 A   2/1975 Stubstad et al.
3,875,595 A   4/1975 Froning
(Continued)

FOREIGN PATENT DOCUMENTS

DE   197 20 241 A1   11/1998
EP   1 374 808 A1    1/2004
WO   WO 2004/098466 A2   11/2004

OTHER PUBLICATIONS

Depuy Spine, Inc., Charité Artificial Disc [online], Nov. 2004 [retrieved on Nov. 18, 2004]. Retrieved from the Internet >URL: http://www.charitedisc.com/.
PRNewswire, FDA Approves First Artificial Disc for Treatment of Low Back Pain, PR Newswire [online], Oct. 26, 2004 [retrieved Nov. 18, 2004]. Retrieved from the Internet >URL: http://www.finance.lycos.com.

(Continued)

*Primary Examiner* — David Isabella
*Assistant Examiner* — Ann Schillinger
(74) *Attorney, Agent, or Firm* — Nutter McClennen & Fish LLP

(57) ABSTRACT

The present invention includes intervertebral prosthetic devices and methods for installing intervertebral prosthetic devices into an intervertebral space. In one embodiment, an intervertebral prosthetic disc includes a superior endplate; an inferior endplate; and at least one protrusion element, wherein at least one of the superior endplate and the inferior endplate is adapted to receive the protrusion element. In another embodiment, the invention includes an intervertebral prosthetic disc having a superior endplate including a core retaining member; an inferior endplate including a core retaining member; and an asymmetric core positioned between the superior endplate and the inferior endplate, wherein the superior endplate and the inferior endplate are adapted to accommodate the core. The present invention also includes an intervertebral prosthetic disc system that includes an intervertebral prosthetic disc and at least one spring element.

17 Claims, 23 Drawing Sheets

(52) U.S. Cl.
CPC ....... 2002/30092 (2013.01); *A61F 2002/30224* (2013.01); *A61F 2002/30365* (2013.01); *A61F 2002/30387* (2013.01); *A61F 2002/30433* (2013.01); *A61F 2002/305* (2013.01); *A61F 2002/30563* (2013.01); *A61F 2002/30565* (2013.01); *A61F 2002/30574* (2013.01); *A61F 2002/30579* (2013.01); *A61F 2002/30594* (2013.01); *A61F 2002/30604* (2013.01); *A61F 2002/30649* (2013.01); *A61F 2002/30662* (2013.01); *A61F 2002/30769* (2013.01); *A61F 2002/30841* (2013.01); *A61F 2002/30878* (2013.01); *A61F 2002/30909* (2013.01); *A61F 2002/443* (2013.01); *A61F 2002/448* (2013.01); *A61F 2210/0014* (2013.01); *A61F 2220/0025* (2013.01); *A61F 2220/0033* (2013.01); *A61F 2220/0041* (2013.01); *A61F 2230/0069* (2013.01); *A61F 2310/00017* (2013.01); *A61F 2310/00023* (2013.01); *A61F 2310/00029* (2013.01); *A61F 2310/00203* (2013.01); *A61F 2310/00239* (2013.01); *A61F 2310/00293* (2013.01); *A61F 2310/00365* (2013.01); *A61F 2310/00796* (2013.01)
USPC ..................................................... 623/17.14

(56) References Cited

U.S. PATENT DOCUMENTS

| | | | |
|---|---|---|---|
| 4,759,769 A | 7/1988 | Hedman et al. | |
| 4,772,287 A | 9/1988 | Ray et al. | |
| 4,904,260 A | 2/1990 | Ray et al. | |
| 4,997,432 A | 3/1991 | Keller | |
| 5,314,477 A | 5/1994 | Marnay | |
| 5,395,317 A | 3/1995 | Kambin | |
| 5,397,364 A | 3/1995 | Kozak et al. | |
| 5,401,269 A | 3/1995 | Büttner-Janz et al. | |
| 5,425,772 A | 6/1995 | Brantigan | |
| 5,425,773 A | 6/1995 | Boyd et al. | |
| 5,458,638 A | 10/1995 | Kuslich et al. | |
| 5,458,642 A | 10/1995 | Beer et al. | |
| 5,549,679 A | 8/1996 | Kuslich | |
| 5,556,431 A | 9/1996 | Büttner-Janz | |
| 5,702,450 A | 12/1997 | Bisserie | |
| 5,716,416 A | 2/1998 | Lin | |
| 5,928,284 A | 7/1999 | Mehdizadeh | |
| 6,019,792 A | 2/2000 | Cauthen | |
| 6,110,210 A | 8/2000 | Norton et al. | |
| 6,143,032 A * | 11/2000 | Schafer et al. | 623/17.11 |
| 6,149,686 A | 11/2000 | Kuslich et al. | |
| 6,159,211 A | 12/2000 | Boriani et al. | |
| 6,179,874 B1 | 1/2001 | Cauthen | |
| 6,206,922 B1 | 3/2001 | Zdeblick et al. | |
| 6,231,609 B1 | 5/2001 | Mehdizadeh | |
| 6,241,769 B1 | 6/2001 | Nicholson et al. | |
| 6,245,108 B1 | 6/2001 | Biscup | |
| 6,368,351 B1 | 4/2002 | Glenn et al. | |
| 6,416,551 B1 | 7/2002 | Keller | |
| 6,419,704 B1 | 7/2002 | Ferree | |
| 6,419,706 B1 * | 7/2002 | Graf | 623/17.16 |
| 6,440,168 B1 | 8/2002 | Cauthen | |
| 6,527,804 B1 * | 3/2003 | Gauchet et al. | 623/17.12 |
| 6,540,785 B1 * | 4/2003 | Gill et al. | 623/17.14 |
| 6,558,390 B2 | 5/2003 | Cragg | |
| 6,572,653 B1 | 6/2003 | Simonson | |
| 6,575,979 B1 | 6/2003 | Cragg | |
| 6,579,321 B1 * | 6/2003 | Gordon et al. | 623/17.16 |
| 6,582,467 B1 * | 6/2003 | Teitelbaum et al. | 623/17.11 |
| 6,582,468 B1 * | 6/2003 | Gauchet | 623/17.16 |
| 6,599,294 B2 | 7/2003 | Fuss et al. | |
| 6,610,093 B1 * | 8/2003 | Pisharodi | 623/17.15 |
| 6,613,091 B1 | 9/2003 | Zdeblick et al. | |
| 6,648,917 B2 | 11/2003 | Gerbec et al. | |
| 6,679,915 B1 | 1/2004 | Cauthen | |
| 6,692,495 B1 | 2/2004 | Zacouto | |
| 6,733,532 B1 * | 5/2004 | Gauchet et al. | 623/17.12 |
| 6,749,635 B1 | 6/2004 | Bryan | |
| 6,770,095 B2 * | 8/2004 | Grinberg et al. | 623/17.14 |
| 6,800,092 B1 | 10/2004 | Williams et al. | |
| 6,835,206 B2 | 12/2004 | Jackson | |
| 6,846,328 B2 * | 1/2005 | Cauthen | 623/17.11 |
| 6,893,465 B2 * | 5/2005 | Huang | 623/17.12 |
| 6,899,735 B2 * | 5/2005 | Coates et al. | 623/17.16 |
| 7,060,097 B2 * | 6/2006 | Fraser et al. | 623/17.11 |
| 7,153,325 B2 * | 12/2006 | Kim et al. | 623/17.15 |
| 2002/0032483 A1 | 3/2002 | Nicholson et al. | |
| 2002/0049497 A1 | 4/2002 | Mason | |
| 2002/0082600 A1 | 6/2002 | Shaolian et al. | |
| 2002/0156528 A1 * | 10/2002 | Gau | 623/17.11 |
| 2002/0183848 A1 | 12/2002 | Ray et al. | |
| 2003/0040802 A1 * | 2/2003 | Errico et al. | 623/17.14 |
| 2003/0069586 A1 * | 4/2003 | Errico et al. | 606/99 |
| 2003/0069639 A1 | 4/2003 | Sander et al. | |
| 2003/0069643 A1 | 4/2003 | Ralph et al. | |
| 2003/0125739 A1 | 7/2003 | Bagga et al. | |
| 2003/0176923 A1 * | 9/2003 | Keller et al. | 623/17.14 |
| 2003/0199982 A1 | 10/2003 | Bryan | |
| 2003/0204261 A1 * | 10/2003 | Eisermann et al. | 623/17.14 |
| 2003/0208273 A1 * | 11/2003 | Eisermann et al. | 623/17.14 |
| 2003/0233146 A1 * | 12/2003 | Grinberg et al. | 623/17.14 |
| 2004/0002759 A1 | 1/2004 | Ferree | |
| 2004/0010316 A1 | 1/2004 | William et al. | |
| 2004/0024461 A1 | 2/2004 | Ferree | |
| 2004/0024462 A1 | 2/2004 | Ferree et al. | |
| 2004/0030387 A1 * | 2/2004 | Landry et al. | 623/16.11 |
| 2004/0030390 A1 | 2/2004 | Ferree | |
| 2004/0030391 A1 | 2/2004 | Ferree | |
| 2004/0034423 A1 * | 2/2004 | Lyons et al. | 623/17.13 |
| 2004/0034426 A1 | 2/2004 | Errico et al. | |
| 2004/0044410 A1 | 3/2004 | Ferree et al. | |
| 2004/0049280 A1 | 3/2004 | Cauthen | |
| 2004/0093082 A1 * | 5/2004 | Ferree | 623/17.11 |
| 2004/0102846 A1 * | 5/2004 | Keller et al. | 623/17.11 |
| 2004/0111155 A1 | 6/2004 | Ferree | |
| 2004/0127991 A1 | 7/2004 | Ferree | |
| 2004/0133281 A1 * | 7/2004 | Khandkar et al. | 623/17.16 |
| 2004/0138749 A1 | 7/2004 | Zucherman et al. | |
| 2004/0138753 A1 | 7/2004 | Ferree | |
| 2004/0143270 A1 | 7/2004 | Zucherman et al. | |
| 2004/0153159 A1 | 8/2004 | Cauthen | |
| 2004/0158254 A1 | 8/2004 | Eisermann | |
| 2004/0158328 A1 | 8/2004 | Eisermann | |
| 2004/0181284 A1 | 9/2004 | Simonson | |
| 2004/0181285 A1 | 9/2004 | Simonson | |
| 2004/0186471 A1 | 9/2004 | Trieu | |
| 2004/0186572 A1 | 9/2004 | Lange et al. | |
| 2004/0186577 A1 | 9/2004 | Ferree | |
| 2004/0193271 A1 | 9/2004 | Fraser et al. | |
| 2004/0193273 A1 * | 9/2004 | Huang | 623/17.12 |
| 2004/0215342 A1 | 10/2004 | Suddaby | |
| 2004/0220668 A1 * | 11/2004 | Eisermann et al. | 623/17.11 |
| 2004/0225362 A1 | 11/2004 | Richelsoph | |
| 2004/0225364 A1 * | 11/2004 | Richelsoph et al. | 623/17.13 |
| 2004/0225365 A1 | 11/2004 | Eisermann et al. | |
| 2004/0225366 A1 | 11/2004 | Eisermann et al. | |
| 2004/0236425 A1 | 11/2004 | Huang | |
| 2004/0243238 A1 | 12/2004 | Arnin et al. | |
| 2004/0243241 A1 * | 12/2004 | Istephanous et al. | 623/17.14 |
| 2004/0254644 A1 | 12/2004 | Taylor | |
| 2004/0260396 A1 | 12/2004 | Ferree et al. | |
| 2005/0027364 A1 | 2/2005 | Kim et al. | |
| 2005/0060035 A1 * | 3/2005 | Errico et al. | 623/17.15 |
| 2005/0261772 A1 * | 11/2005 | Filippi et al. | 623/17.13 |
| 2006/0015183 A1 * | 1/2006 | Gilbert et al. | 623/17.11 |
| 2006/0095132 A1 * | 5/2006 | Kirschman | 623/17.14 |

OTHER PUBLICATIONS

Spine-Health, Inc., Total Disc Replacement-Charite™ Artificial Disc [online], 1999-2004 Spine-health.com [retrieved Nov. 18, 2004]. Retrieved from the Internet >URL: http://www.spine-health.com.

* cited by examiner

INTERVERTEBRAL PROSTHETIC DISC

BACKGROUND OF THE INVENTION

The human spinal column consists of discrete, sequentially coupled bones, i.e., vertebrae, cushioned by cartilaginous spacers, i.e., intervertebral discs, disposed between opposing vertebral bone endplates. Intervertebral discs are generally elastic, allowing the spine to retain a high degree of flexibility. When a disc, or a portion of a disc, wears out or is injured, the disc cannot function normally and the failed disc can cause pain to a patient or limit the patient's activities. Therefore, surgery is often recommended when an intervertebral disc fails, for example, due to disease, infection, deformity, or fracture. Surgery can sometimes help to reduce attendant pain and restore at least some level of activity to the patient. Surgery can include implantation of an artificial disc or other prosthetic devices that restore the height of the spinal column and a natural angle between the adjacent vertebrae. For example, surgery can include spinal fusion or disc replacement. Spinal fusion can be effective in reducing pain, but it limits the range of motion of the spine and it can result in transfer of extra stress to discs above and below the fusion site. Generally, known artificial discs offer several benefits over spinal fusion, including pain reduction and a potential to avoid premature degeneration at adjacent levels of the spine by maintaining normal spinal motion.

Commonly, implantation of an artificial disc is performed using an anterior approach. For example, two surgeons typically work together in performing an anterior approach artificial disc implantation. A general or vascular surgeon approaches the spine through an incision in the abdomen and carefully moves internal organs and blood vessels to provide access to the spine. A spine surgeon then removes the damaged disc, prepares the intervertebral space for implantation of the artificial disc, and inserts the artificial disc into the intervertebral space. Post-operative complications can include abdominal wall hematoma, vascular injury, retrograde ejaculation, and gastrointestinal injury following implantation of an artificial disc.

A need exists for intervertebral prosthetic devices and methods for placing intervertebral prosthetic devices that overcome or minimize the above-referenced problems.

SUMMARY OF THE INVENTION

The present invention includes intervertebral prosthetic devices and methods for installing intervertebral prosthetic devices into an intervertebral space.

In one embodiment, the intervertebral prosthetic disc includes a superior endplate; an inferior endplate; and at least one protrusion element, wherein at least one of the superior endplate and the inferior endplate is adapted to receive the protrusion element. In another embodiment, an intervertebral prosthetic disc includes a superior endplate; an inferior endplate; a core positioned between the superior endplate and the inferior endplate; and at least one protrusion element, wherein at least one of the superior endplate and the inferior endplate is adapted to receive the protrusion element.

The invention also includes a method for installing a prosthetic disc into an intervertebral space. The method includes inserting a first endplate into an intervertebral space; joining at least one protrusion element to the first endplate within the intervertebral space, thereby forming a first endplate assembly. Also, the method can include inserting a first endplate into an intervertebral space; joining at least one protrusion element to the first endplate within the intervertebral space, thereby forming a first endplate assembly; seating the first endplate assembly onto a first vertebral bone endplate; inserting a second endplate assembly into the intervertebral space and seating the second endplate assembly onto a second vertebral bone endplate; and positioning a core between the first endplate assembly and the second endplate assembly.

In another embodiment, the invention includes an intervertebral prosthetic disc having a superior endplate including a core retaining member; an inferior endplate including a core retaining member; and an asymmetric core positioned between the superior endplate and the inferior endplate, wherein the superior endplate and the inferior endplate are adapted to accommodate the core. The intervertebral prosthetic disc can also include at least one core plate.

In yet another embodiment, an intervertebral prosthetic disc includes a superior endplate; an inferior endplate; and a core including a plurality of core modules positioned between the superior endplate and the inferior endplate, wherein the superior endplate and the inferior endplate are adapted to accommodate the core. The core modules can mate or abut and thereby constrain movement relative to one another, e.g., lateral-medial movement can be constrained.

The present invention also includes an intervertebral prosthetic disc system. The system comprises an intervertebral prosthetic disc including two plates adapted for insertion between two vertebrae and a core which cooperates with at least one plate at an articular surface; and at least one spring element adapted for insertion between the two vertebrae. The intervertebral prosthetic disc and the at least one spring element can be adapted for insertion into an intervertebral space by a posterior or a posterior-lateral surgical approach. For example, the intervertebral prosthetic disc is sized for insertion, e.g., piece-wise insertion of components thereof, into an intervertebral space using a posterior or posterior-lateral approach.

The present invention also includes an intervertebral prosthetic disc system which includes an intervertebral prosthetic disc including two plates adapted for insertion between two vertebrae and at least one spring element adapted for insertion between the two vertebrae. The intervertebral prosthetic disc and the at least one spring element can be adapted for insertion into an intervertebral space by a posterior or a posterior-lateral surgical approach. For example, the intervertebral prosthetic disc is sized for insertion, e.g., piece-wise insertion of components thereof, into an intervertebral space using a posterior or posterior-lateral approach. In one embodiment, the intervertebral prosthetic disc includes a first plate which includes a ball component and a second plate that includes a socket component and wherein the socket component receives the ball component.

In another embodiment, an intervertebral prosthetic disc includes a superior endplate assembly including a plurality of superior endplate components; an inferior endplate assembly including a plurality of inferior endplate components; and a core which includes a plurality of core modules which cooperate with at least one of the superior endplate assembly and the inferior endplate assembly at an articular surface. The superior endplate assembly and the inferior endplate assembly can be adapted for posterior or posterior-lateral insertion between two vertebrae. For example, the intervertebral prosthetic disc is sized for insertion, e.g., piece-wise insertion of components thereof, into an intervertebral space using a posterior or posterior-lateral approach.

By practicing the present invention, an intervertebral prosthetic disc can be inserted using a posterior or a posterior-lateral approach. For example, in one embodiment, the intervertebral prosthetic disc includes at least one protrusion element whereby the surface area of the prosthetic disc that is presented to the vertebral bone endplate is increased. By joining at least one protrusion element to an endplate within the intervertebral space, generally smaller prosthetic disc components (e.g., endplates or endplate components) can be used and therefore a posterior or posterior-lateral approach can be used to install the prosthetic disc.

In another embodiment, the intervertebral prosthetic disc includes a core wherein the core includes a plurality of core modules positioned between a superior endplate and an inferior endplate and wherein the superior endplate and inferior endplate are adapted to accommodate the core. By using a core which includes a plurality of core modules, generally smaller core modules can be used and therefore a posterior or posterior-lateral approach can be used to install the prosthetic disc.

In still another embodiment, the intervertebral prosthetic disc includes an asymmetric core positioned between a superior endplate having a core retaining member and the inferior endplate having a core retaining member. Intervertebral prosthetic discs which include a core retaining member can include asymmetric cores and can be made smaller than prosthetic discs that do not have core retaining members. Thus, a posterior or posterior-lateral approach can be used to install the prosthetic disc.

In yet another embodiment, the invention includes a intervertebral prosthetic disc system that includes an intervertebral prosthetic disc and at least one spring element. Spring elements can thus be used, for example, to increase the surface area of the system and to provide additional support. Thus, in one embodiment, the intervertebral prosthetic disc can be smaller than a disc used for an anterior surgical operation and therefore the system can be used for posterior or posterior-lateral installation of the intervertebral prosthetic disc.

A posterior or a posterior-lateral procedure to intervertebral disc replacement is typically less invasive than an anterior procedure. Complications related to anterior procedures can be reduced or eliminated by practicing the present invention. In some embodiments, the services of a vascular surgeon needed to access the intervertebral disc space are reduced or eliminated.

By practicing the present invention, a surgeon using a guidewire placement method can obtain precise location of a prosthetic disc's endplates relative to the vertebral bodies. The present invention can provide the surgeon with the ability to finely adjust the location of the intervertebral disc to ensure proper disc function. By practicing the invention, pieces of an endplate can be connected with relative ease within the intervertebral space. As a result, smaller devices can be inserted through smaller exposures and assembled in vivo.

The intervertebral prosthetic discs of the present invention can have a generally larger surface area for contact with the vertebral bone endplates than would be expected in a device inserted using a posterior or posterior-lateral approach. A generally larger surface area for contact with the vertebral bone endplates can reduce or eliminate subsidence of the intervertebral prosthetic disc.

The intervertebral prosthetic discs of the present invention can provide for translation motion as well as rotation motion when surgically installed in the spinal column. Practice of the present invention can also expand patient indications that can be treated using the herein-described intervertebral prosthetic disc by restoring spinal stability without having to rely on the natural anatomy. For example, practice of the present invention can restore spinal stability without having to rely on the facets of the spine to limit motion. In one embodiment, spring elements can be used to resist excessive rotation and translation.

DETAILED DESCRIPTION OF THE INVENTION

Figure 1A:
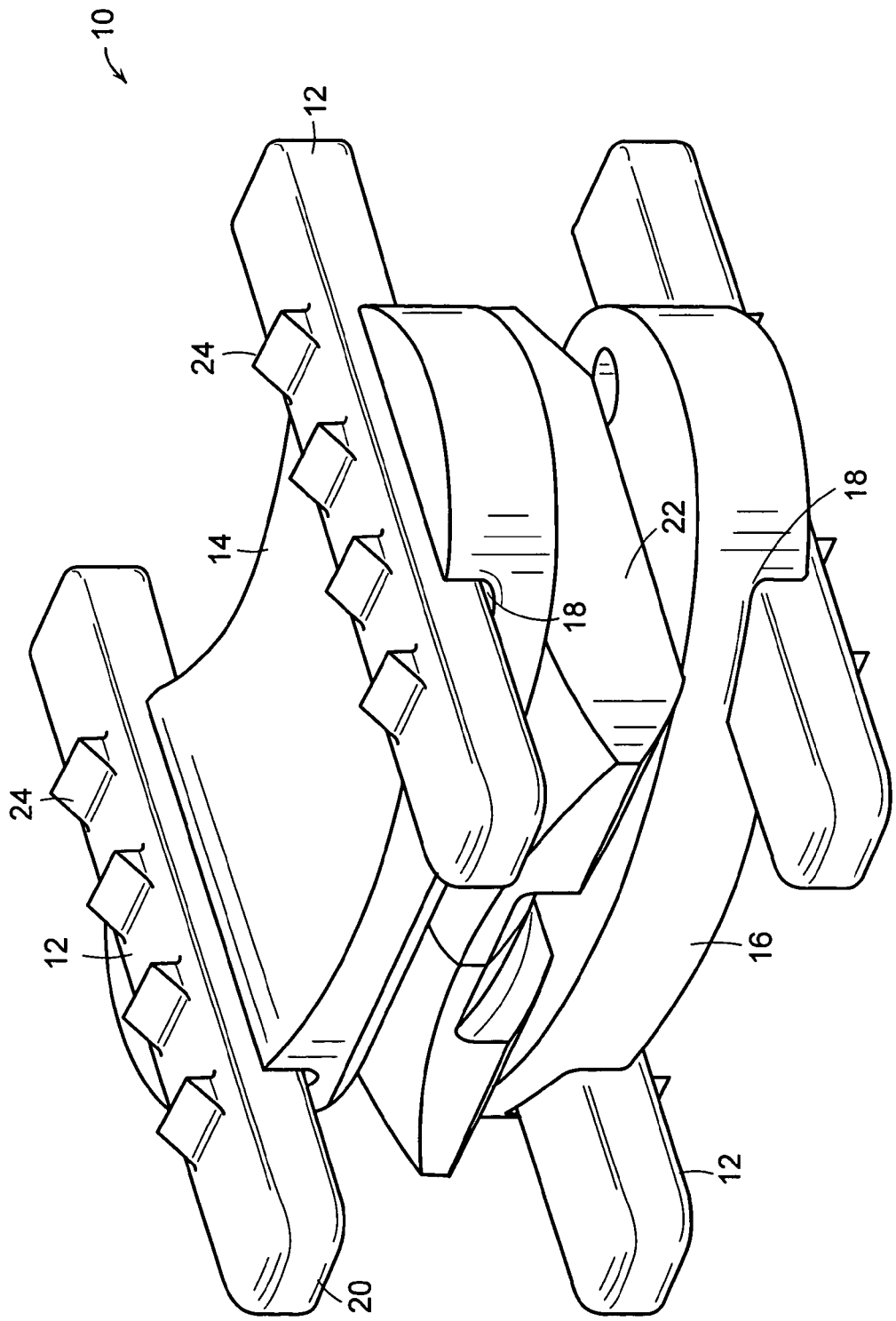
FIG. 1A is a perspective view of an example of an assembled intervertebral prosthetic disc that includes protrusion elements.

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

The present invention includes an intervertebral prosthetic disc. In one embodiment, an intervertebral prosthetic disc includes a superior endplate; an inferior endplate; and at least one protrusion element, wherein at least one of the superior endplate and the inferior endplate is adapted to receive the protrusion element. In another embodiment, the present invention includes an intervertebral prosthetic disc which includes a superior endplate; an inferior endplate; a core positioned between the superior endplate and the inferior endplate; and at least one protrusion element, wherein at least one of the superior endplate and the inferior endplate is adapted to receive the protrusion element. Protrusion elements can be used to increase the surface area of an endplate that is presented to a vertebral bone endplate. In other embodiments, an intervertebral prosthetic disc includes a superior endplate; an inferior endplate; a core positioned between the superior endplate and the inferior endplate; and at least one protrusion element, wherein at least one of the superior endplate and the inferior endplate is adapted to receive the protrusion element FIG. 1A is a perspective view of an example of assembled intervertebral prosthetic disc 10 that includes protrusion elements 12. As illustrated, endplates 14 and 16 are adapted to receive protrusion elements 12. In one embodiment, at least one of the superior endplate and the inferior endplate is adapted to receive protrusion element 12. For example, protrusion element 12 can fit into groove 18 defined by endplate 14 or 16. In one embodiment, groove 18 contains a dovetail feature or interlocking feature for interaction with a corresponding structure on protrusion element 12. Protrusion element 12 can also contain bulleted lead-in feature 20 that facilitates joining protrusion element 12 to the endplate. Bulleted lead-in feature 20 is shown in FIG. 1A as a tapering of one end of protrusion element 12.

In one embodiment, a plurality of protrusion elements 12 can be joined to endplates 14 and 16. In other embodiments not illustrated, endplates 14 and 16 are adapted to receive only a single protrusion element 12. In one embodiment, at least one of endplates 14 and 16 includes a protrusion element. In other embodiments, only one of endplates 14 and 16 is adapted to receive one or more protrusion elements 12. Core 22, which can also include a plurality of core modules as described infra, is shown positioned between endplates 14 and 16.

Protrusion elements 12 include vertebral bone endplate anchor elements 24. Endplates 14 and 16 can also include similar vertebral bone endplate anchor elements. In general, at least one of endplates 14 and 16 and protrusion elements 12 can include vertebral bone endplate anchor elements. The anchor elements are generally capable of penetrating a vertebral bone endplate. Examples of anchor elements can include, but are not limited to, keels, spikes, teeth, fins, and pegs. In some embodiments, at least one of endplates 14 and 16 and protrusion elements 12 can include a textured surface that facilitates bone growth. For example, the textured surface can include at least one member selected from the group consisting of porous beading, hydroxyapatite, and mesh. In one embodiment, at least one of endplates 14 and 16 and protrusion elements 12 can include an osteoinductive material. Osteoinductive materials suitable for use include, for example, titanium, cobalt-chromium, nitinol, stainless steel, polyethylene, polyester, polyurethane, silicone, polycarbonate, zirconia, alumina, hydroxyapatite, tricalcium phosphate, collagen, bone morphogenic proteins, demineralized bone matrices, and growth factors.

Figure 1B:
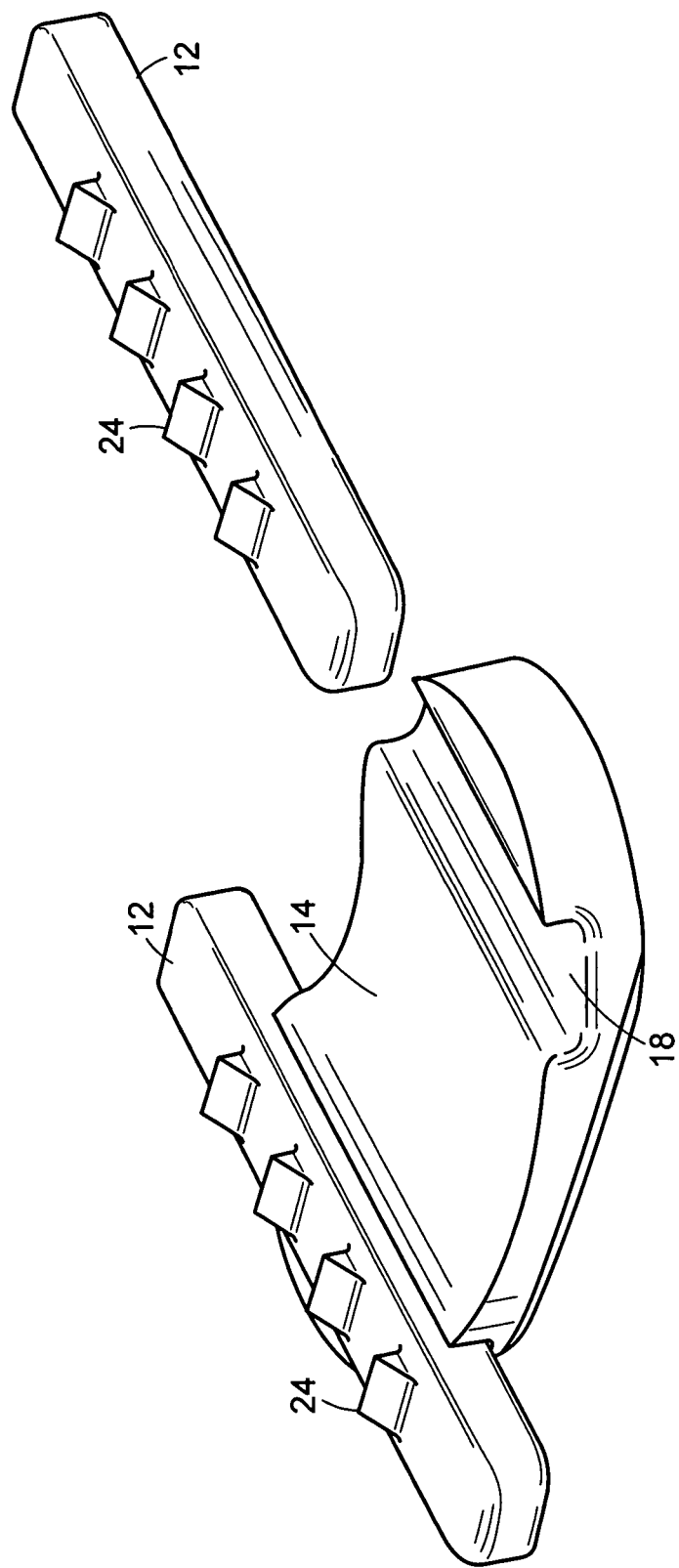
FIG. 1B is a perspective view of an example of assembly of an intervertebral prosthetic disc endplate that includes protrusion elements.

FIG. 1B shows a perspective view of assembly of intervertebral prosthetic disc endplate 14 that includes protrusion elements 12.

Figure 1C:
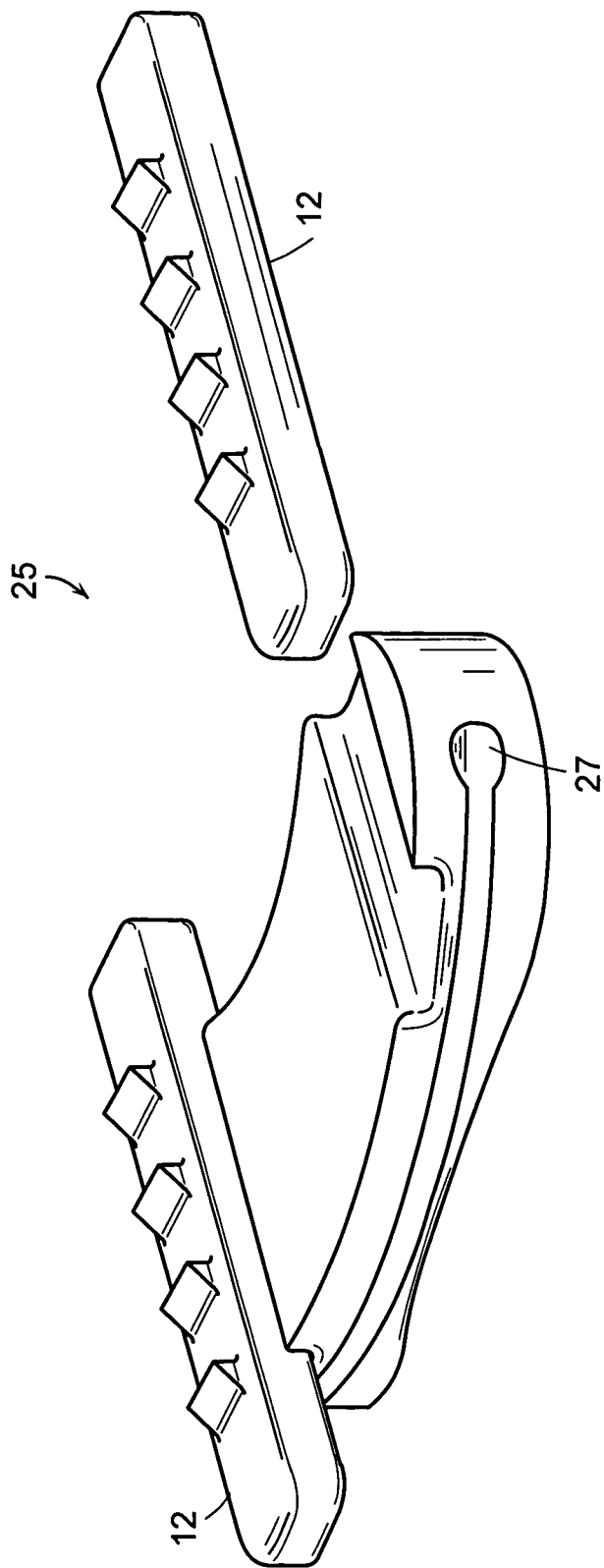
FIG. 1C is a perspective view of an example of assembly of an intervertebral prosthetic disc endplate that includes protrusion elements and a guidewire channel.

FIG. 1C illustrates assembly of intervertebral prosthetic disc endplate 25 that includes protrusion elements 12 and guidewire channel 27, described further infra.

Figure 2:
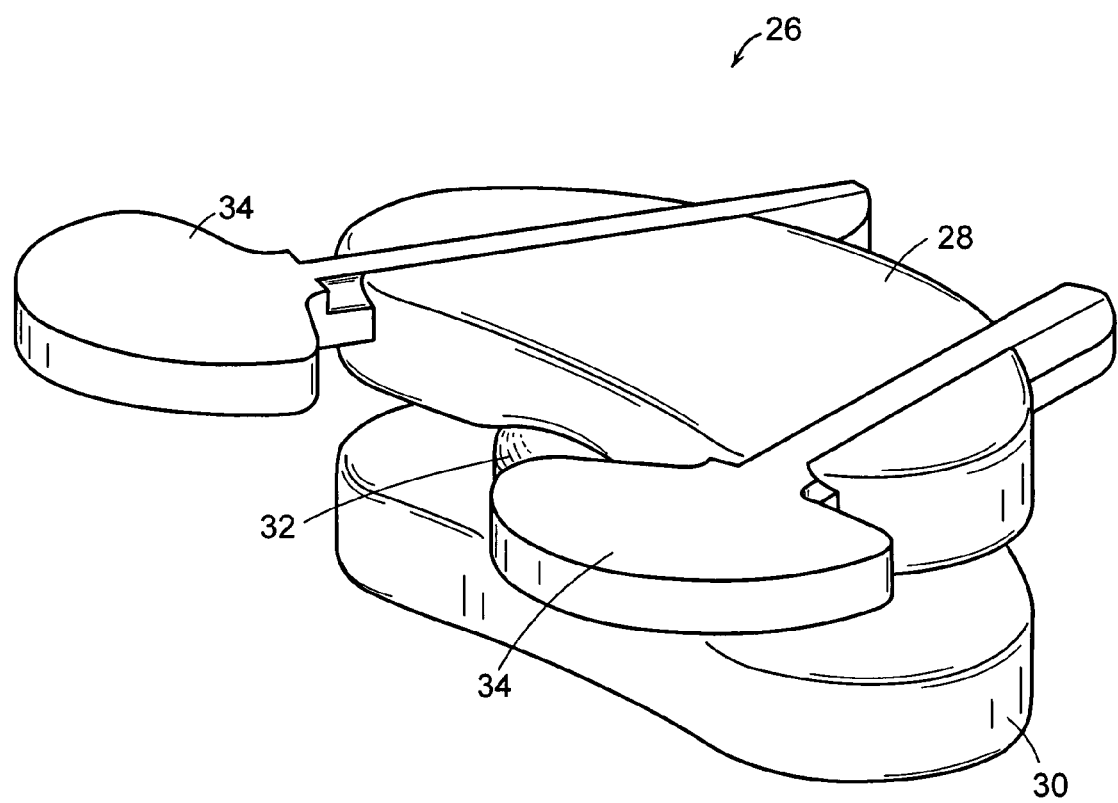
FIG. 2 is a perspective view of another example of an assembled intervertebral prosthetic disc that includes protrusion elements.

FIGS. 1A, 1B, and 1C depict protrusion elements 12 as rails. In other embodiments, protrusion elements 12 have other sizes or geometries. For example, FIG. 2 illustrates an alternative embodiment of an assembled intervertebral prosthetic disc. Intervertebral prosthetic disc 26 contains endplates 28 and 30, core 32, and protrusion elements 34. In one embodiment not illustrated, intervertebral prosthetic disc 26 can also include vertebral bone endplate anchor elements. As demonstrated in FIG. 2, protrusion elements 34 can have a variety of shapes and sizes to increase the surface area of the endplate assembly that is presented to the vertebral bone endplate.

In other embodiments, intervertebral prosthetic disc endplates which include ball and socket components can be used. For example, in one embodiment, a first endplate includes a ball component and a second endplate includes a socket component for receiving the ball component and at least one of the endplates includes a protrusion element.

Figure 3A:
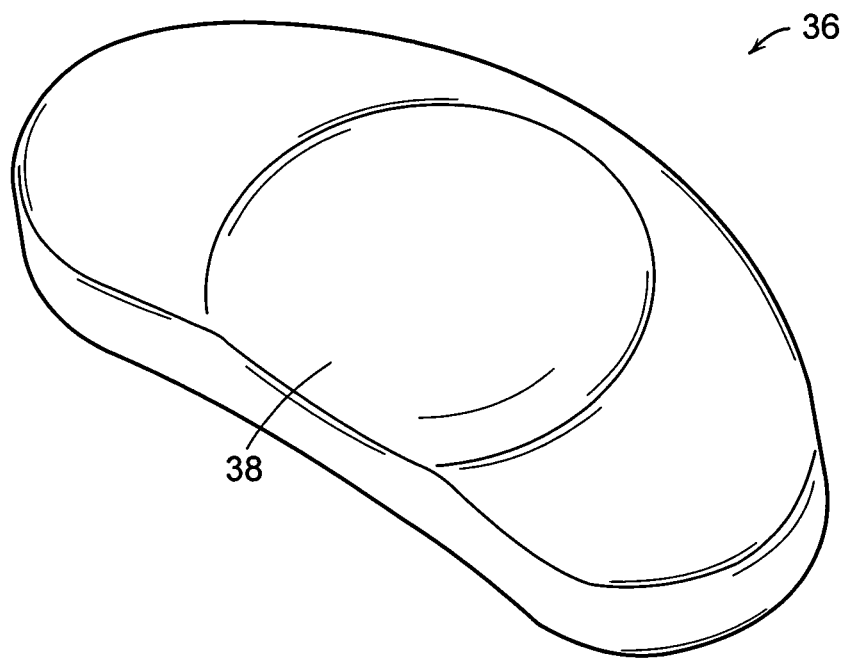
FIGS. 3A-3D are perspective views of endplate embodiments.

FIG. 3A is a perspective view of endplate 36 which includes truncated spherical recess 38 to accommodate the core, e.g., core 32. In some embodiments, endplate 36 can be adapted to receive a protrusion element, e.g., protrusion element 12 or 34.

Figure 3B:
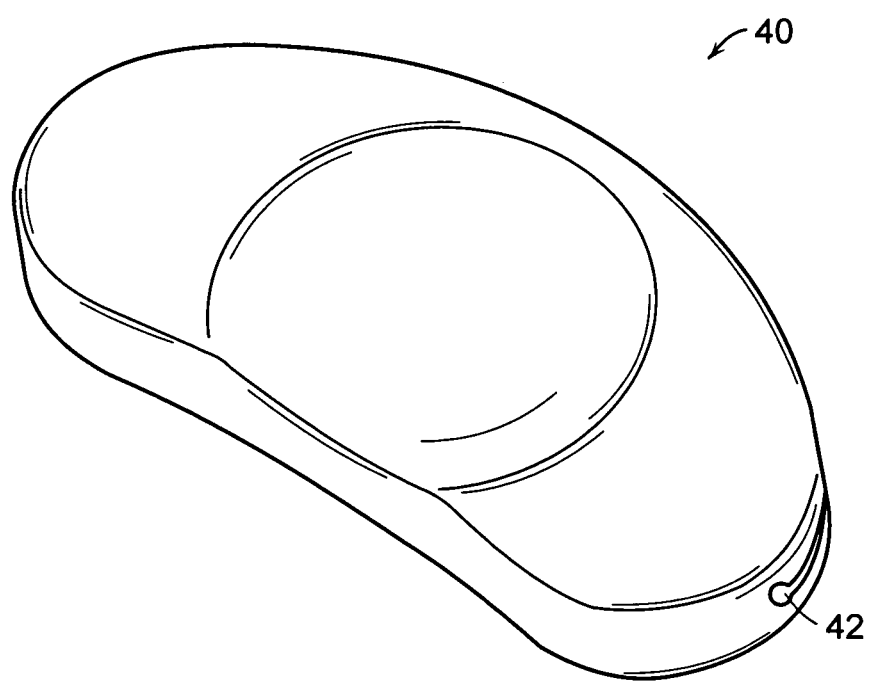
Figure 3C:
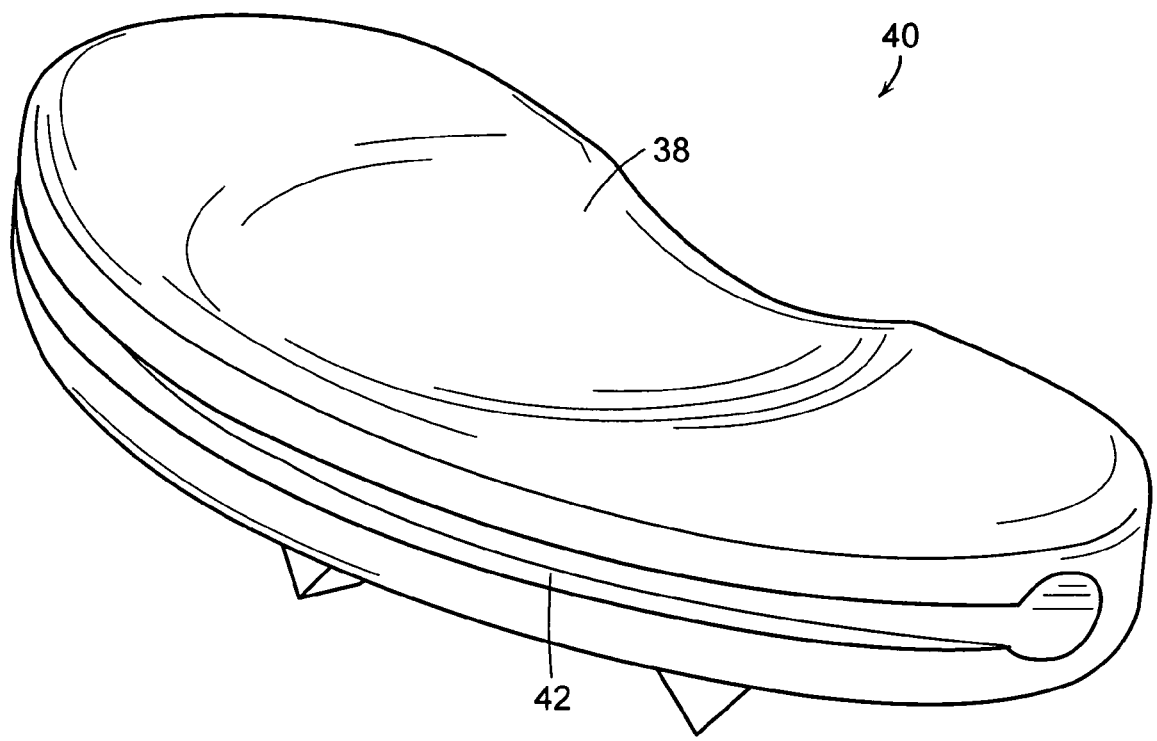
Figure 3D:
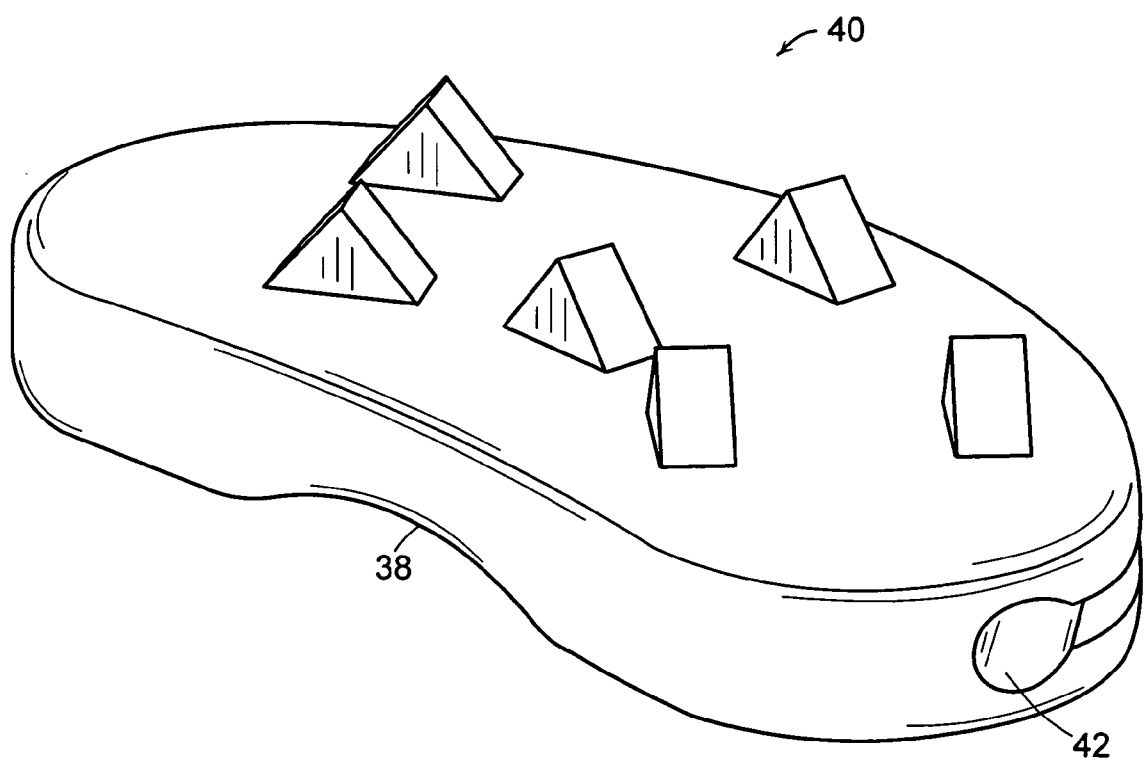

FIG. 3B illustrates endplate 40 according to one embodiment of the present invention wherein endplate 40 defines guidewire channel 42. FIGS. 3C and 3D also illustrate views of one embodiment of the present invention wherein endplate 40 defines guidewire channel 42. In general, endplates, e.g., endplates 14 and 16 or endplates 28 and 30, can be adapted to receive a guidewire. Intervertebral prosthetic disc components adapted to receive a guidewire and methods for installing intervertebral prosthetic disc components using a guidewire are further described in U.S. patent application Ser. No. 11/055,566, entitled "Intervertebral Prosthetic Disc and Method for Installing Using a Guidewire," filed on even date herewith, the entire contents of which are incorporated herein by reference.

FIGS. 4A-4G are perspective views of an intervertebral prosthetic disc and components thereof according to various embodiments of the present invention.

Figure 4A:
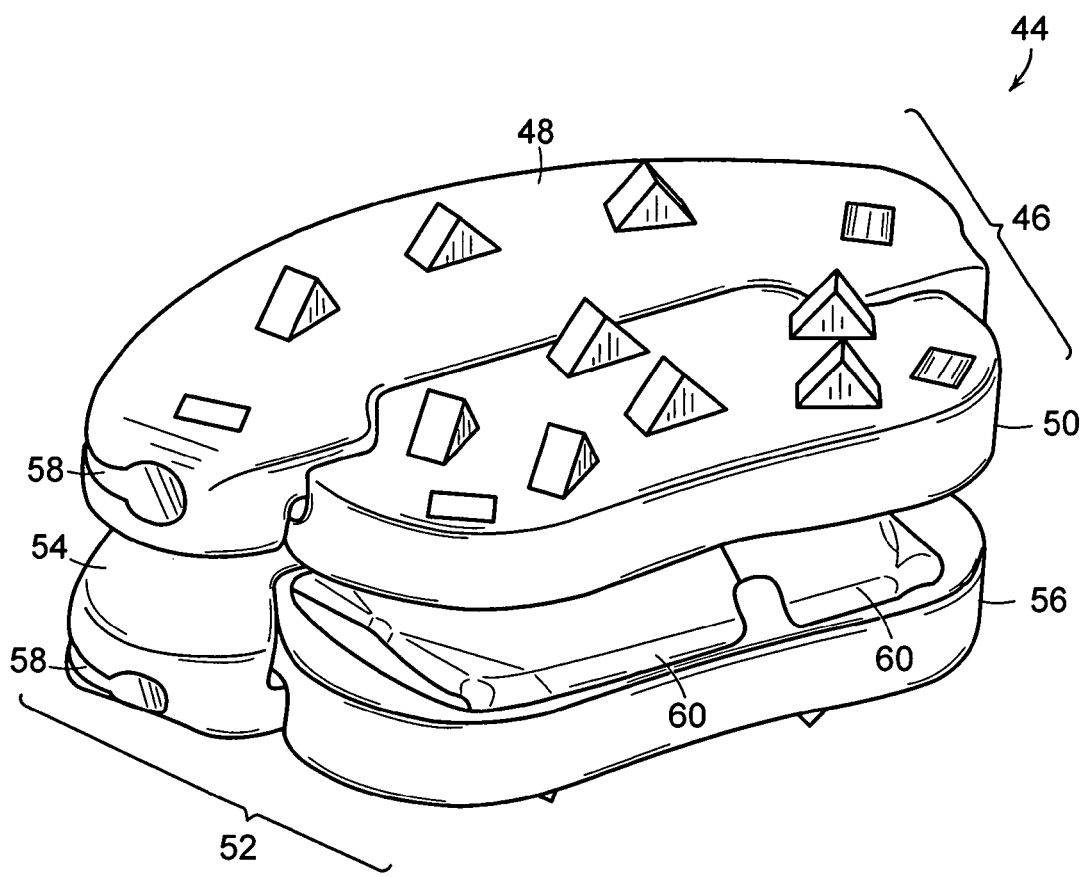
FIGS. 4A-4G are perspective views of an intervertebral prosthetic disc and components thereof according to various embodiments of the present invention.

FIG. 4A shows an example of an intervertebral prosthetic disc 44 that includes first endplate 46 that includes anterior plate 48 and posterior plate 50 and second endplate 52 that includes anterior plate 54 and posterior plate 56. Anterior plate 48 and posterior plate 50 can be adapted for affixation to one another. In one embodiment, anterior plate 48 and posterior plate 50 interlock to form endplate 46. In one embodiment not illustrated, anterior plate 48 and posterior plate 50 are affixed using a dovetail joint. Though not illustrated in FIG. 4A, anterior plate 48 and posterior plate 50 can also, or alternatively, be fixed together with a fastener such as, for example, a peg, snap, or screw. Likewise, anterior plate 54 and posterior plate 56 can be adapted for affixation to one another.

As shown in FIG. 4A, anterior plates 48 and 54 define guidewire channels 58. Guidewire channels 58 can lie along anterior edges of anterior plates 48 and 54. Anterior plate 48 and posterior plate 50 can be substantially similar to anterior plate 54 and posterior plate 56, respectively, but can differ in the number and configuration of recesses, described infra, that are defined thereby. Core modules 60 can be accommodated by recesses defined in endplates 46 and 52. For example, as illustrated in FIG. 4B, core modules 60 can be accommodated by recesses 62 defined in posterior plates 50 and 56.

Figure 4B:
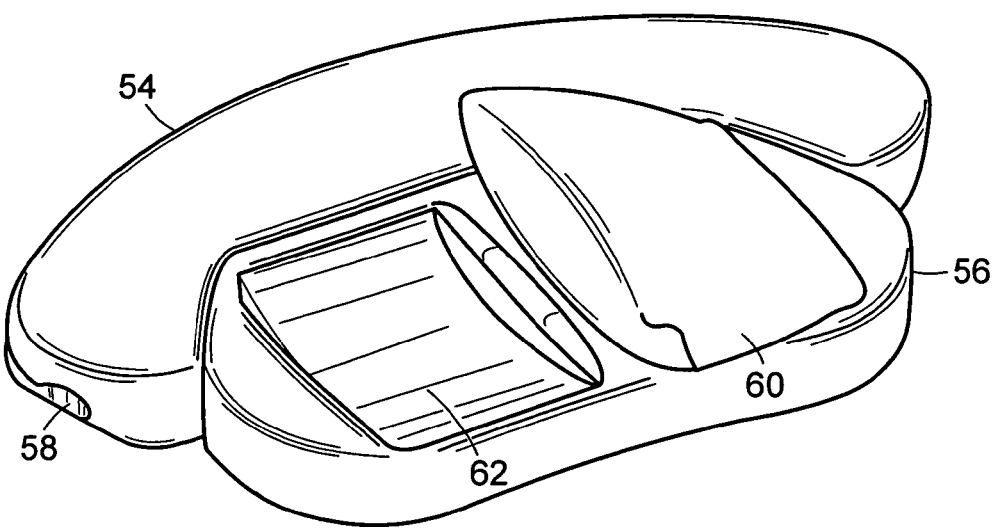

FIG. 4B shows the intervertebral prosthetic disc of FIG. 4A, partially assembled. Posterior plate 56 is illustrated as having truncated cylindrical recess 62 wherein a core module similar to core module 60 can be accommodated and wherein core modules 60, once installed, will mate or abut.

Figure 4C:
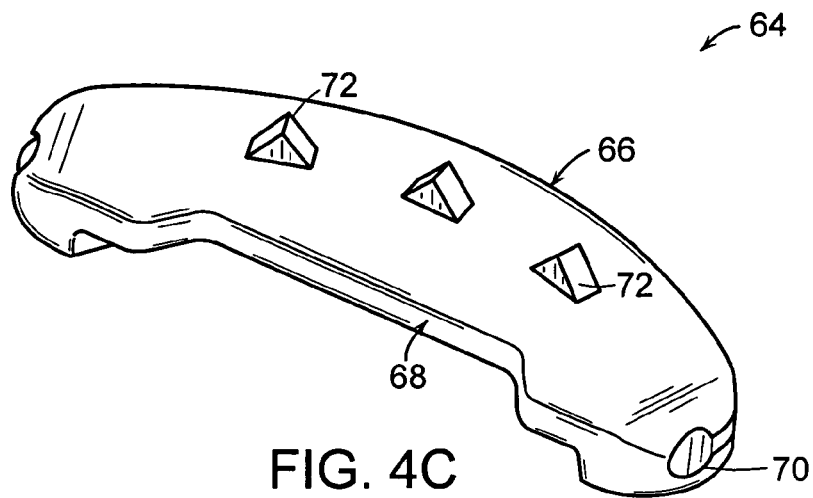
Figure 4D:
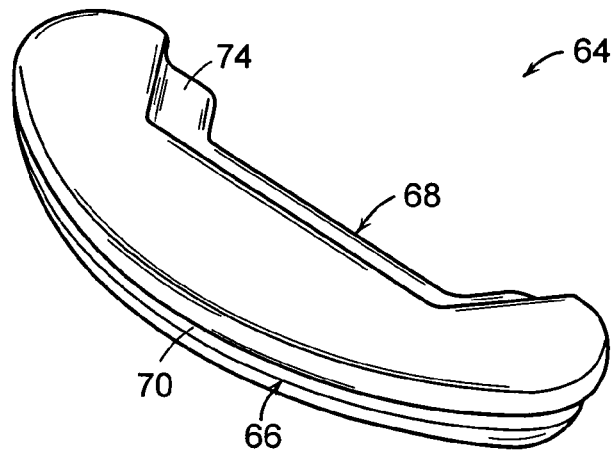

FIGS. 4C and 4D illustrate anterior plate 64 according to one embodiment of the present invention. Anterior plate 64 includes anterior edge 66 and posterior edge 68. As shown in FIGS. 4C and 4D, anterior plate 64 defines guidewire channel 70. Guidewire channel 70 can lie along anterior edge 66. In one embodiment, the guidewire channel can lie along the posterior edge of the anterior plate. In another embodiment, anterior plate 64 does not include guidewire channel 70.

Anterior plate 64 can include vertebral bone endplate anchor elements 72. Suitable vertebral bone endplate anchor elements are described supra. Anterior plate 64 can also define interface 74, e.g., a cantilever or ledge, for joining anterior plate 64 with a posterior plate, thereby forming an endplate, e.g., endplate 46 or 52. In one embodiment not illustrated, interface 74 is a dovetail interface.

Figure 4E:
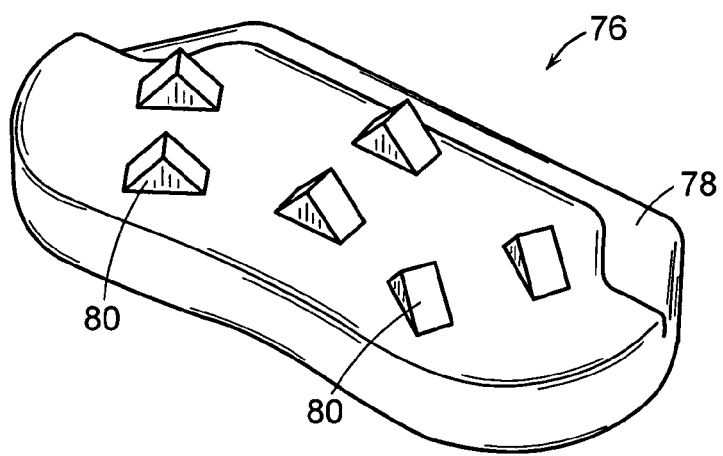

FIG. 4E illustrates a posterior plate according to one embodiment of the present invention. Posterior plate 76 can define interface 78, e.g., a cantilever, ledge or dovetail, for joining posterior plate 76 with an anterior plate, e.g., anterior plate 64, thereby forming an endplate, e.g., endplate 46 or 52. While not illustrated, in one embodiment, posterior plate 76 can define a guidewire channel. Posterior plate 76 can include vertebral bone endplate anchor elements 80. Suitable vertebral bone endplate anchor elements are described supra.

Figure 4F:
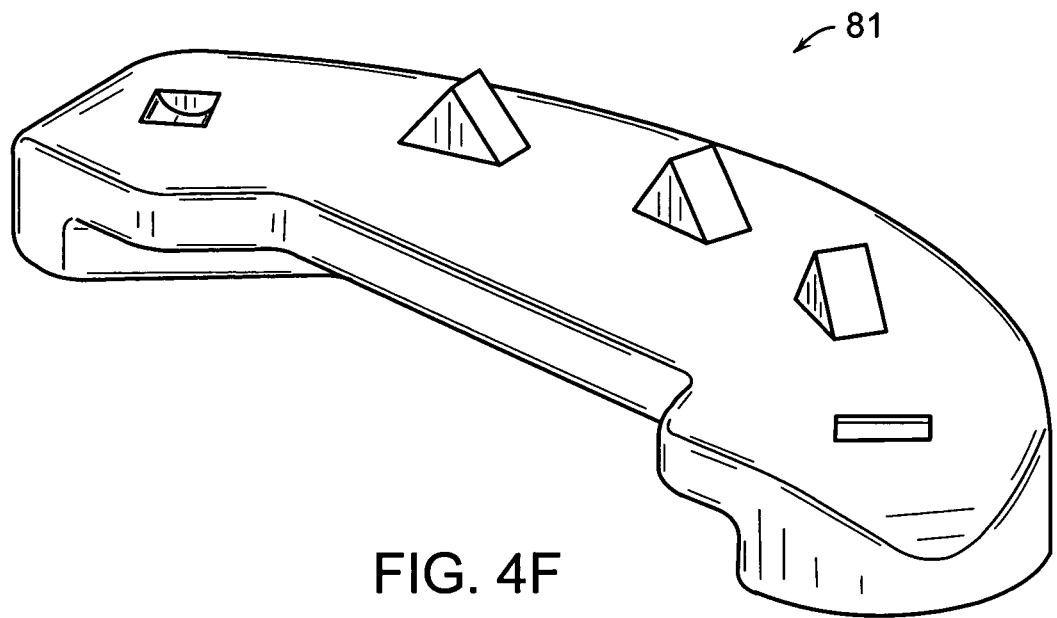
Figure 4G:
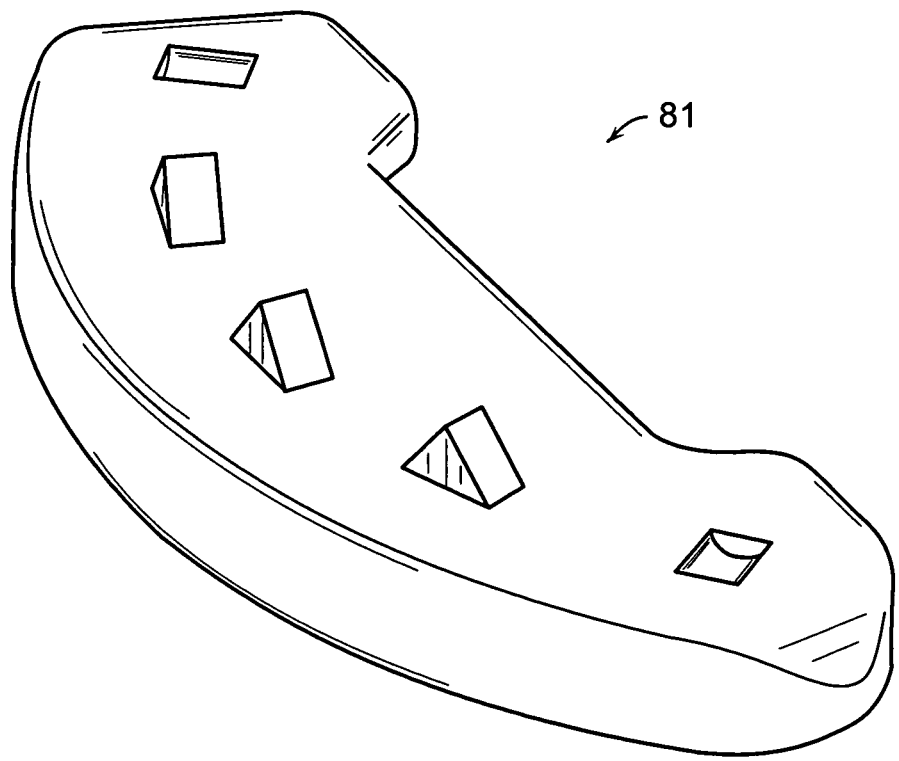

FIGS. 4F and 4G illustrate one embodiment wherein anterior plate 81 does not include a guidewire channel.

The superior and inferior endplates and any components thereof described herein can be constructed of any of the materials known in the art for use in a prosthetic disc. For example, the endplates and any components thereof can be constructed of medical grade cobalt chromium alloy. Protrusion elements can be constructed of similar materials.

The intervertebral prosthetic disc can also include a core positioned between the superior endplate and the inferior endplate. The core is typically separated from the vertebral bone endplates by the superior and inferior endplates. In one embodiment, the core is resilient. The core can be constructed of any of the materials known in the art for use in a prosthetic disc core. In a preferred embodiment, the core is constructed of a medical grade plastic with good sliding properties with respect to the endplate materials. In one embodiment, the core is polyethylene, for example, high density polyethylene.

As illustrated in FIG. 4A, the core can include a plurality of core modules. Core modules are constructed of the materials described supra. In one embodiment, the core includes two core modules 60. In one aspect of the invention, core modules 60 are adapted so as to constrain movement relative to one another such as lateral-medial movement. For example, in one embodiment, core modules 60 mate or abut, thereby constraining movement relative to one another, e.g., lateral-medial movement can be constrained.

In one embodiment, one or, both of the endplates, for example, endplates 14 and 16 of FIG. 1A, endplates 28 and 32 of FIG. 2, or endplates 46 and 52 of FIG. 4A, are adapted to accommodate the core. For example, at least one of the endplates can define at least one recess to accommodate the core. In one embodiment, the recess constrains the core from substantial lateral-medial movement relative to the superior endplate and the inferior endplate. The recess can assume a variety of geometries. For example, as illustrated in FIG. 4B, recess 62 is a truncated cylindrical recess, e.g., a truncated cylindrical recess with a cylinder axis that lies along a lateral-medial line with respect to the endplate. In the embodiment illustrated in FIG. 3A, recess 38 is a truncated spherical recess.

In some embodiments, the superior endplate of the intervertebral prosthetic disc includes an anterior plate (e.g., a first anterior plate) and a first posterior plate (e.g., a first posterior plate), and the anterior plate or the posterior plate defines a recess to accommodate the core. For example, as illustrated in FIG. 4A, the posterior plate can define a recess to accommodate the core. In some embodiments, the inferior endplate includes an anterior plate (e.g., a second anterior plate) and a posterior plate (e.g., a second posterior plate), and the anterior plate or the posterior plate defines a recess to accommodate the core. For example, as illustrated in FIG. 4A, the posterior plate can define a recess to accommodate the core. The core can include a plurality of core modules and, in those cases, the superior endplate or the inferior endplate can define a plurality of recesses to accommodate the plurality of core modules. However, in some embodiments, the superior endplate or the inferior endplate can define a single recess to accommodate a plurality of core modules.

The present invention includes an intervertebral prosthetic disc wherein the superior endplate defines a truncated spherical recess and the inferior endplate defines a plurality of truncated cylindrical recesses, as illustrated by FIG. 4A. The present invention also includes an intervertebral prosthetic disc wherein the inferior endplate defines a truncated spherical recess and the superior endplate defines a plurality of truncated cylindrical recesses; as the superior/inferior orientation of FIG. 4A is interchangeable, this embodiment is also illustrated by FIG. 4A.

The invention also includes a method for installing a prosthetic disc into an intervertebral space. The method includes inserting a first endplate into an intervertebral space; joining at least one protrusion element to the first endplate within the intervertebral space, thereby forming a first endplate assembly; seating the first endplate assembly onto a first vertebral bone endplate; inserting a second endplate assembly into the intervertebral space and seating the second endplate assembly onto a second vertebral bone endplate; and positioning a core between the first endplate assembly and the second endplate assembly. In one embodiment, the second endplate assembly is a one-component plate. In another embodiment, the second endplate assembly includes a plate and at least one protrusion element.

In another embodiment, the method includes inserting a first endplate into an intervertebral space; joining at least one protrusion element to the first endplate within the intervertebral space, thereby forming a first endplate assembly; seating the first endplate assembly onto a first vertebral bone endplate; inserting a second endplate assembly into the intervertebral space and seating the second endplate assembly onto a second vertebral bone endplate. In one embodiment, one of the endplates includes a ball component and the other endplate includes a socket component for receiving the ball component.

The method includes the step of joining at least one protrusion element to the first endplate. As described supra, protrusion elements can be used to increase the surface area of an endplate that is presented to a vertebral bone endplate. In one embodiment, a protrusion element is joined to the first endplate within the intervertebral space. By joining the protrusion element to the first endplate within the intervertebral space, small elements can be introduced through the surgical incision, e.g., elements suitably sized for a posterior or posterior-lateral surgical approach, while a high surface area implantation can be made to the vertebral bone endplate. In one embodiment, a plurality of protrusion elements is joined to the first endplate. For example, the protrusion element can fit into a groove defined by the endplate. In one embodiment, the groove defined by the plate contains a dovetail feature or interlocking feature for interaction with a corresponding structure on the protrusion element. A protrusion element can also contain a bulleted lead-in feature that facilitates joining the element to the plate. FIGS. 1B and 1C, described supra, illustrate assembly of intervertebral prosthetic disc endplates that include protrusion elements 12.

In other embodiments, intervertebral prosthetic disc endplates which include ball and socket components can be used. For example, in one embodiment, a first endplate includes a ball component and a second endplate includes a socket component for receiving the ball component wherein at least one of the first and second endplates includes an anterior plate and a posterior plate. In one embodiment, at least one of the anterior plate and the posterior plate includes a guidewire channel.

Figure 5:
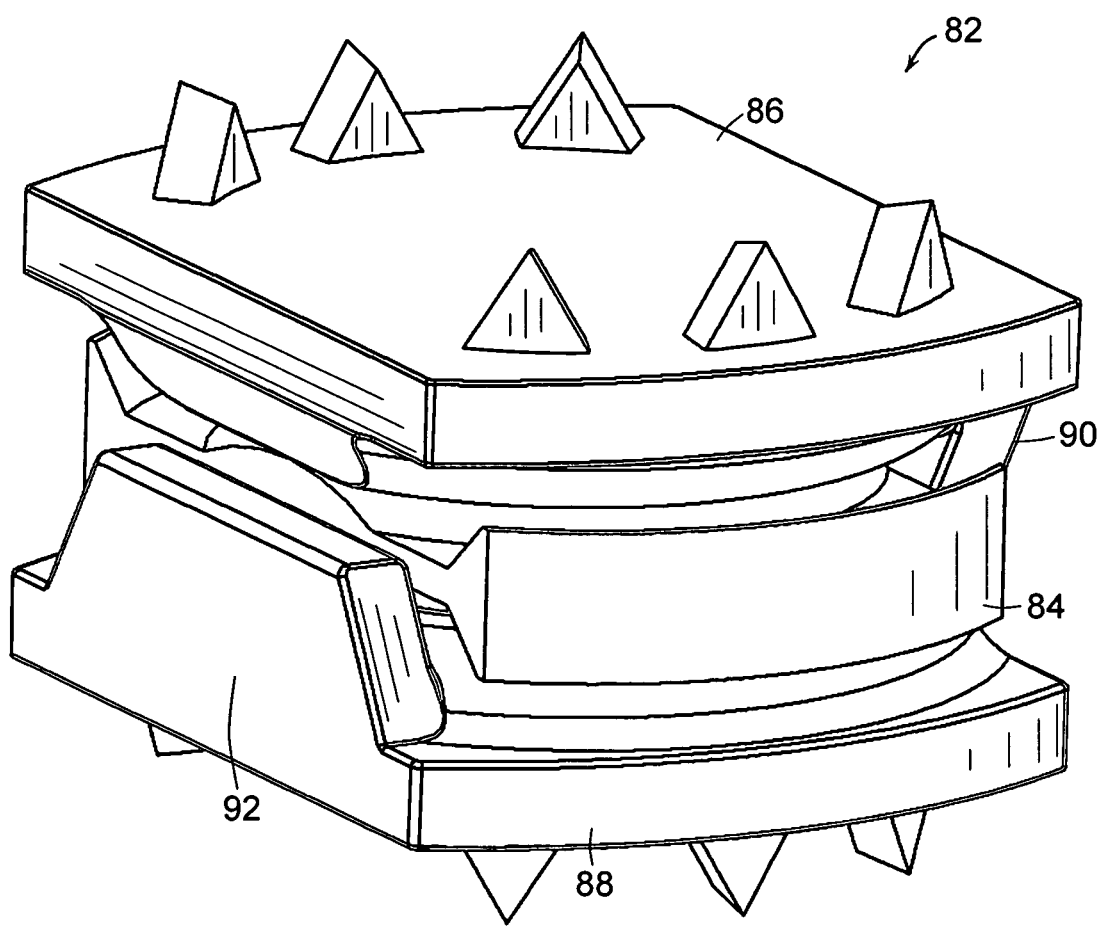
FIG. 5 is a perspective view of an example of an assembled intervertebral prosthetic disc that includes an asymmetric core and endplates which include core retaining members.

FIG. 5 is a perspective view of an example of assembled intervertebral prosthetic disc 82 that includes asymmetric core 84 and endplates 86 and 88 which include core retaining members 90. In one aspect, the present invention includes an intervertebral prosthetic disc having superior endplate 86 including core retaining member 90; inferior endplate 88 including core retaining member 92; and asymmetric core 84 positioned between superior endplate 86 and inferior endplate 88, wherein superior endplate 86 and inferior endplate 88 are adapted to accommodate asymmetric core 84. In one embodiment, intervertebral prosthetic disc 82 is sized for insertion, e.g., piece-wise insertion of components thereof, into an intervertebral space using a posterior or posterior-lateral approach.

Figure 6:
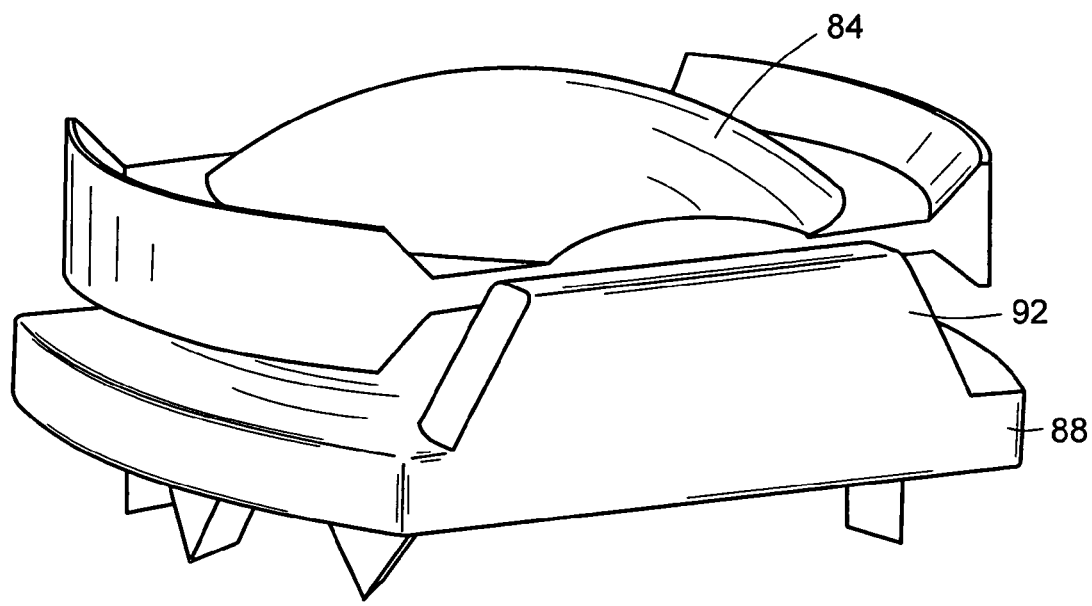
FIG. 6 is a perspective view of an example of a partially assembled intervertebral prosthetic disc showing an asymmetric core placed on an endplate.

FIG. 6 is a perspective view of partially assembled intervertebral prosthetic disc 82 showing asymmetric core 84 placed on endplate 88.

Figure 7A:
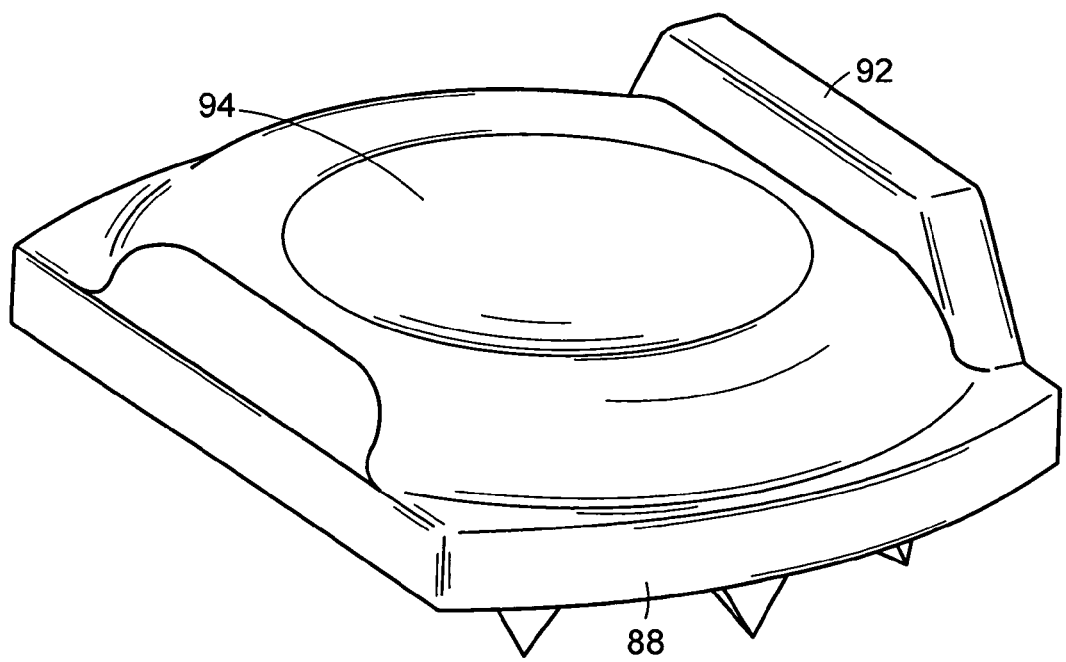
FIG. 7A is a perspective view of an example of an endplate which includes a core retaining member and a recess for accommodation of a core.

FIG. 7A is a perspective view of endplate 88 which includes core retaining member 92 and recess 94, i.e., a truncated spherical recess, for accommodation of core 84. In one embodiment, core retaining member 92 is an integral component of endplate 88. In another embodiment, core retaining member 92 is a modular component affixed to endplate 88. Core retaining members such as core retaining members 90 and 92 can prevent the core from rotating. The core retaining members can also assist to keep the core centered between endplates 86 and 88 and also to prevent expulsion of the core from the prosthetic disc.

Figure 7B:
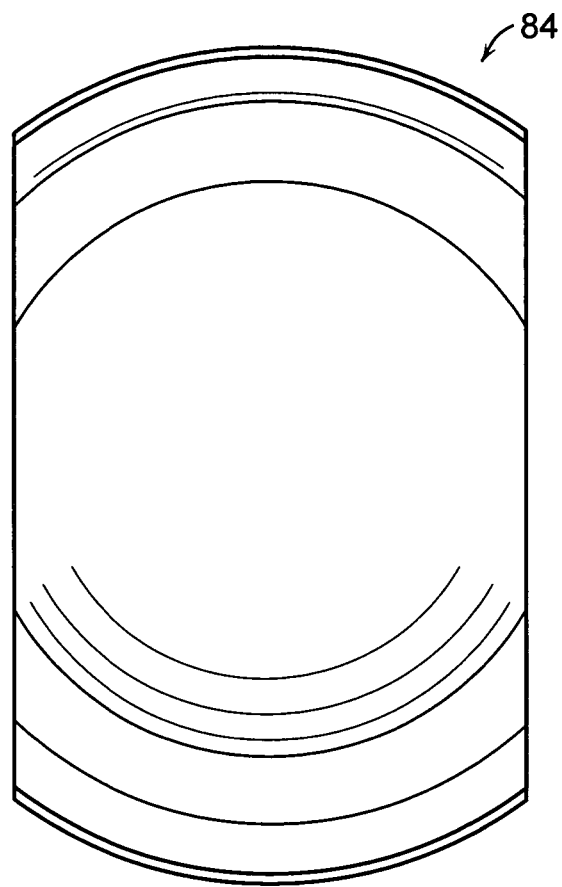
FIGS. 7B-7D are views of asymmetric cores according to various embodiments of the present invention.
Figure 7C:
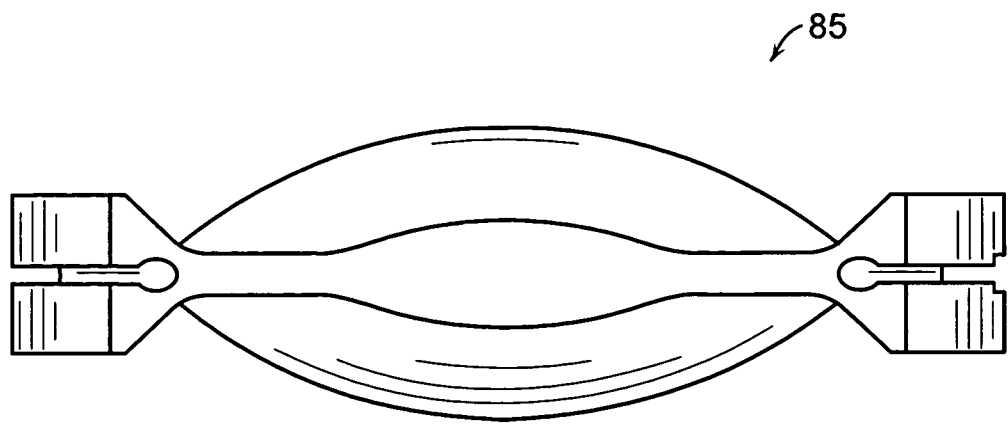
Figure 7D:
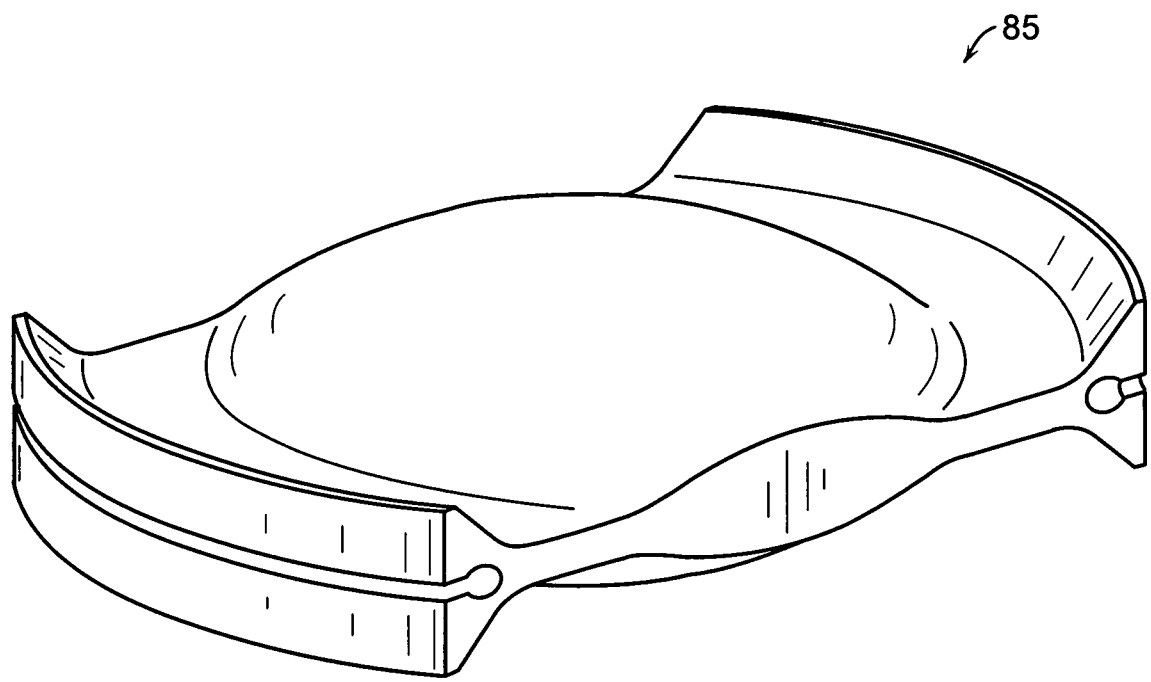

FIG. 7B is a top view of core 84 also illustrated in FIGS. 5 and 6. FIGS. 7C and 7D illustrate core 85 according to one embodiment of the present invention. In one embodiment, core 85 can be used in conjunction with endplate 88 illustrated in FIG. 7A.

Figure 7E:
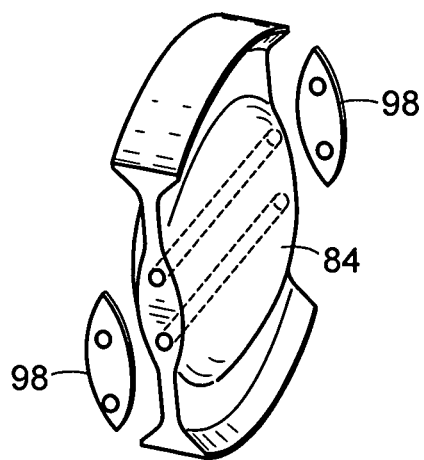
FIGS. 7E and 7F are views of examples of the use of core plates to constrain an asymmetric core.
Figure 7F:
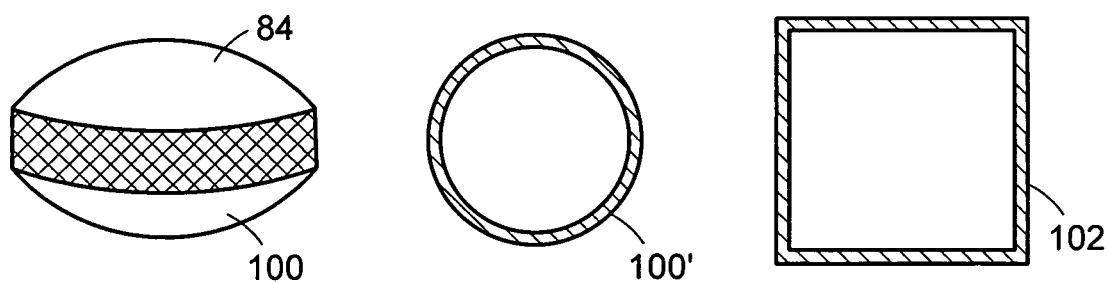

FIGS. 7E and 7F are views of examples of the use of core plates to constrain an asymmetric core. FIG. 7E illustrates asymmetric core 84 having side wall core plates 98. Side wall core plates 98 can be attached using, for example, bolts and/or screws. FIG. 7F illustrates rigid band core plates 100 and 102 for attachment to asymmetric core 84. Rigid band core plates, such as rigid band core plates 100 and 102, can take various shapes depending on the installation orientation on core 84. Rigid band core plates can include, for example, circular, rectangular or square bands. Rigid band core plates are typically constructed of, for example, tanium, stainless steel, cobalt chrome, or other stiff biocompatible materials.

In one embodiment, intervertebral prosthetic disc 82 includes at least one core plate such as side wall core plates 98 or rigid band core plates 100 and 102. Core plates 98, 100 and 102 can be used to prevent side expansion of the core due to compression load. Core plates 98, 100 and 102 can also be used to prevent creep of the core material. Core plates can be constructed of any of the medical grade materials suitable for use in artificial discs and having suitable strength such as, for example, a metal such as cobalt chromium alloy.

As shown in FIG. 7E, asymmetric core 84 can be characterized by two parallel side walls 96 that truncate an otherwise round core. Asymmetric core 84 can cooperate with at least one of endplates 86 and 88 at an articular surface.

Figure 8A:
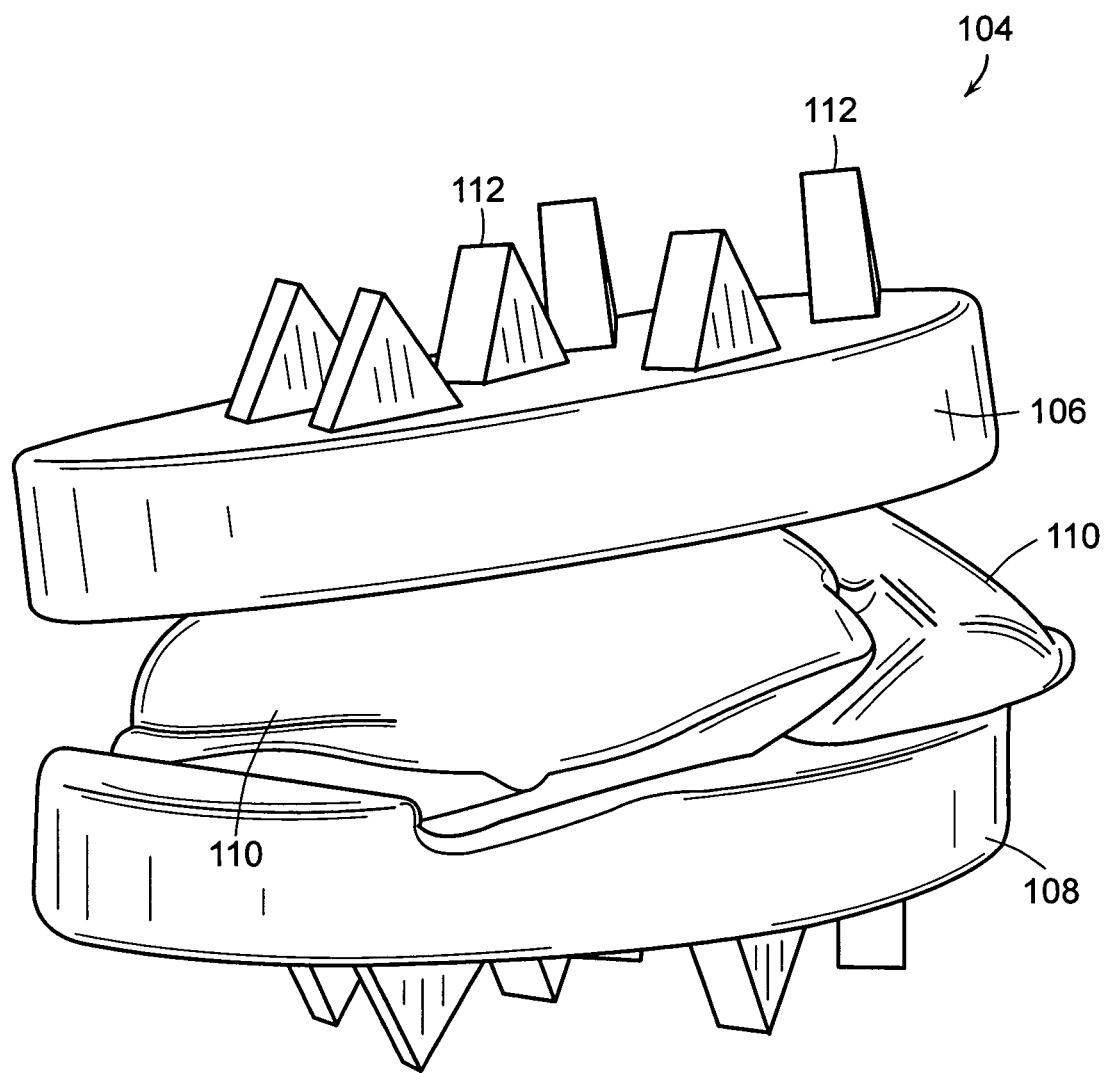
FIGS. 8A and 8B are perspective views of an example of an assembled intervertebral prosthetic disc having a core which includes a plurality of core modules.
Figure 8B:
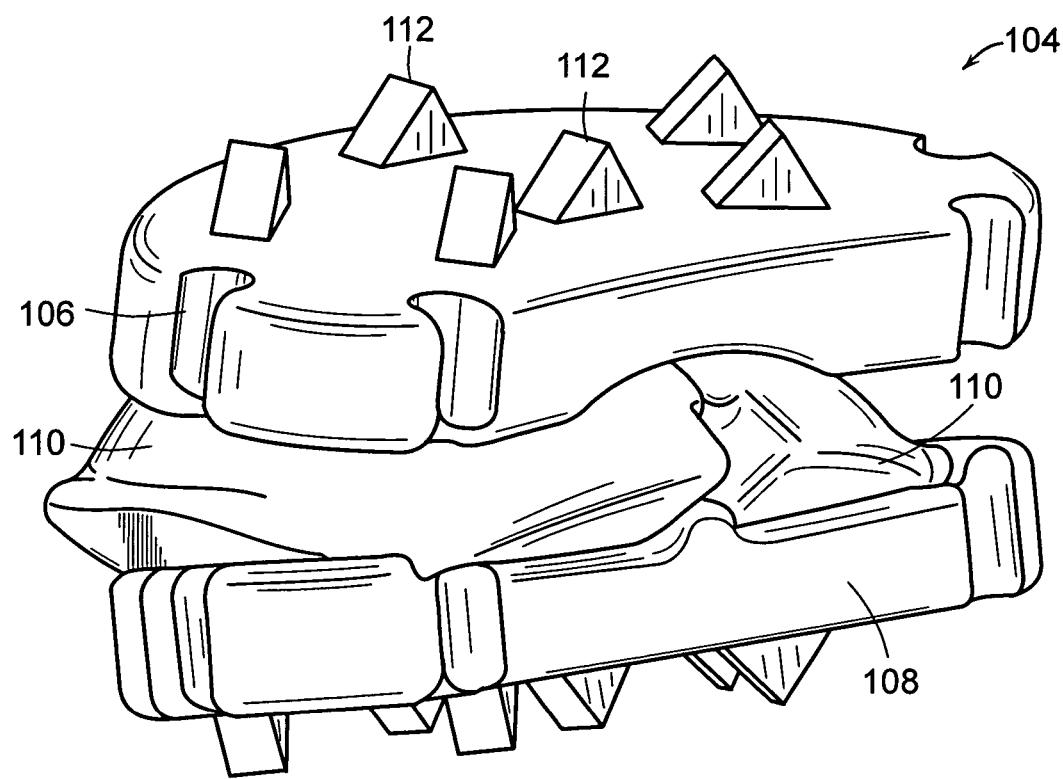

FIGS. 8A and 8B are perspective views of an example of assembled intervertebral prosthetic disc 104 having a core which includes a plurality of core modules 110. Endplates 106 and 108 sandwich core modules 110. Intervertebral prosthetic disc 104 also includes vertebral bone endplate anchor elements 112, described supra.

Figure 9A:
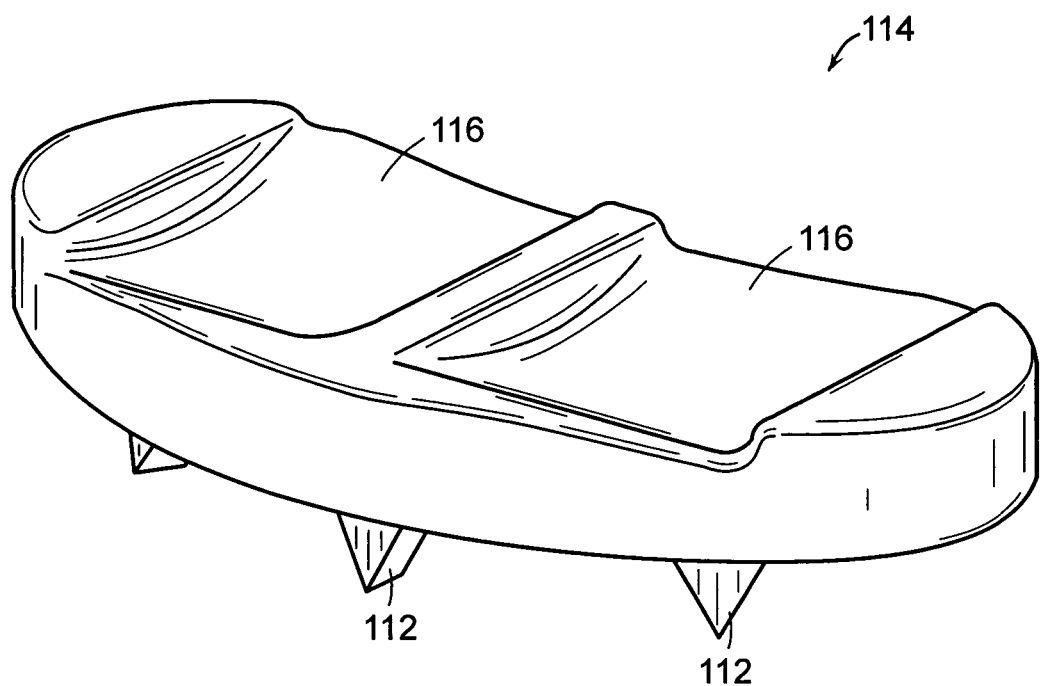
FIGS. 9A and 9B are perspective views of examples of endplates adapted to accommodate cores which include a plurality of core modules.

FIG. 9A is a perspective view of an example of endplate 114 adapted to accommodate a core which includes a plurality of core modules. Endplate 114 includes two truncated cylindrical recesses 116 to accommodate the core.

Figure 9B:
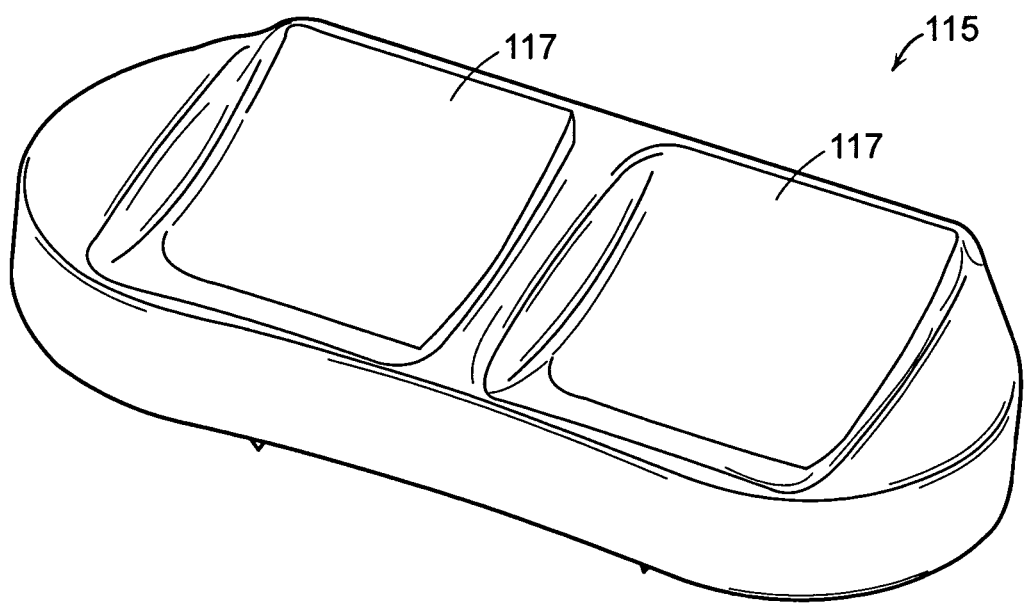

FIG. 9B is a perspective view of an example of endplate 115 adapted to accommodate a core which includes a plurality of core modules. Endplate 115 includes two truncated cylindrical recesses 117 to accommodate the core.

In one embodiment of the invention, intervertebral prosthetic disc 104 includes superior endplate 106; inferior endplate 108; and a core including a plurality of core modules 110 positioned between superior endplate 106 and inferior endplate 108, wherein superior endplate 106 and the inferior endplate 108 are adapted to accommodate the core. Superior endplate 106 and inferior endplate 108 can be adapted to accommodate the core similar to that described supra. For example, at least one of superior endplate 106 and inferior endplate 108 can define at least one recess, e.g., recess 116, to accommodate core modules 110. The recess can be a truncated cylindrical recess, e.g., truncated cylindrical recess 116 with a major axis that lies along a lateral-medial line with respect to endplate 114. In another embodiment illustrated in FIG. 3A, the recess is a truncated spherical recess. Core modules 110 can mate or abut when installed in the intervertebral disc and thereby constrain movement relative to one another, e.g., lateral-medial movement. In a preferred embodiment, the intervertebral prosthetic disc is sized for insertion, e.g., piece-wise insertion of components thereof, into an intervertebral space using a posterior or posterior-lateral approach.

Figure 10:
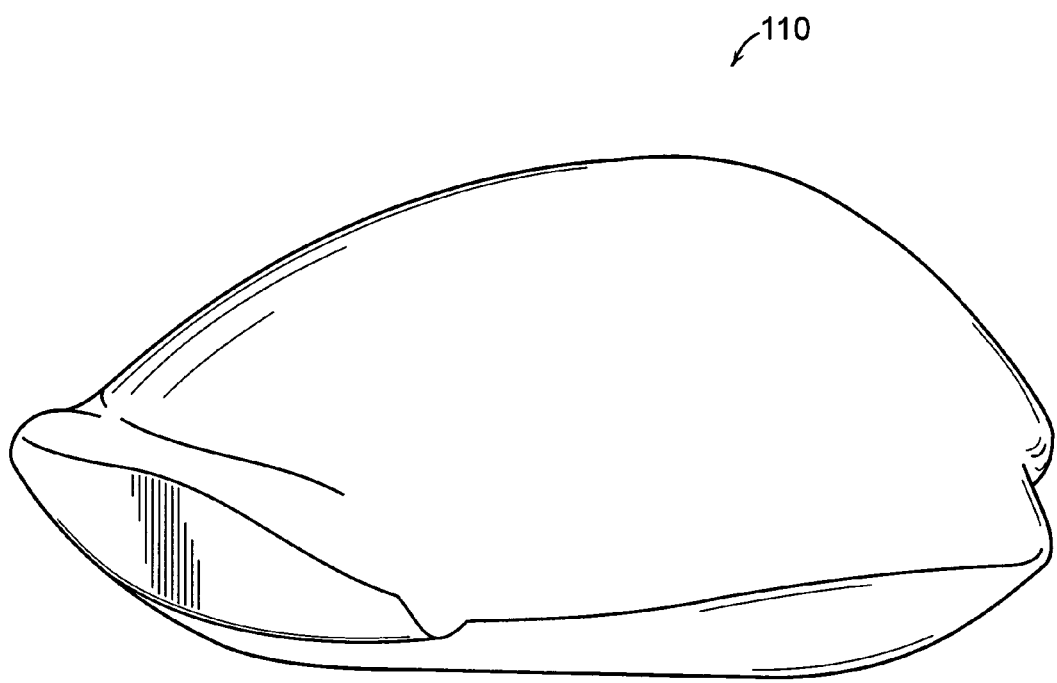
FIG. 10 illustrates an example of a core module.

FIG. 10 illustrates an example of core module 110.

Figure 11:
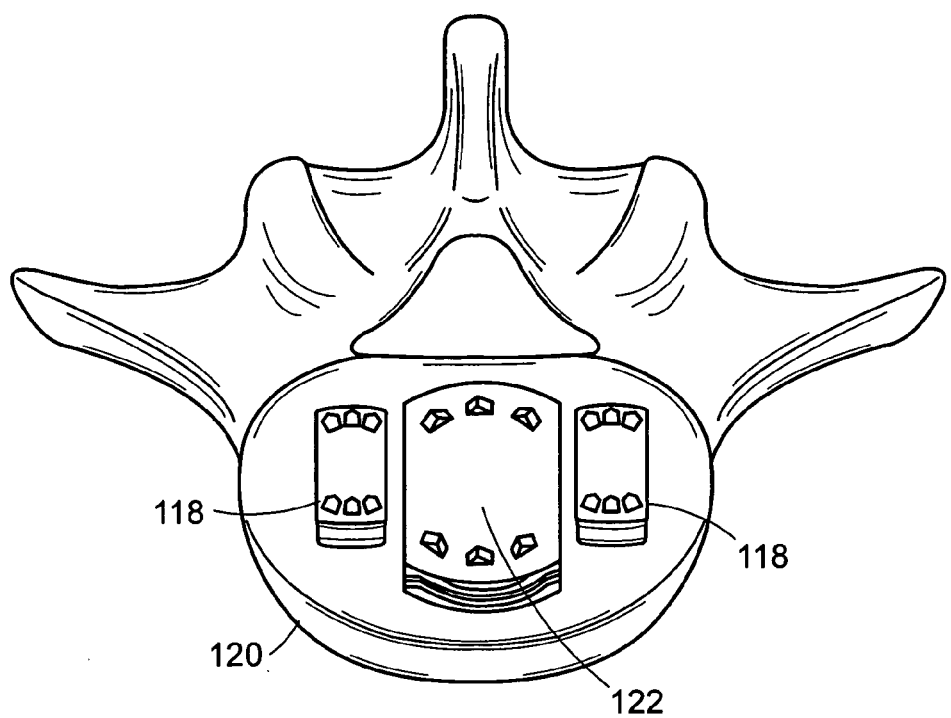
FIG. 11 is a view of an example of an intervertebral prosthetic disc system that includes two spring elements on a vertebral body.
Figure 12:
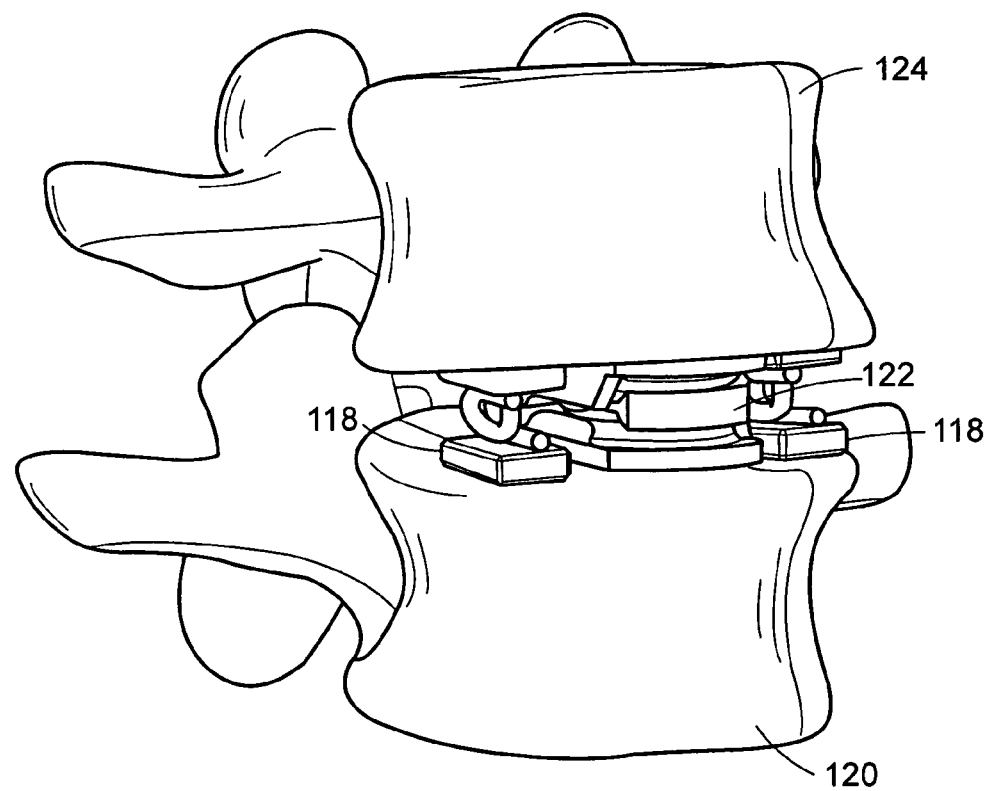
FIG. 12 is a perspective view of the intervertebral prosthetic disc system shown in FIG. 11.

The present invention also includes an intervertebral prosthetic disc system. FIGS. 11 and 12 are views of an example of an intervertebral prosthetic disc system that includes two spring elements 118 on vertebral body 120. The system also includes intervertebral prosthetic disc 122.

Figure 13:
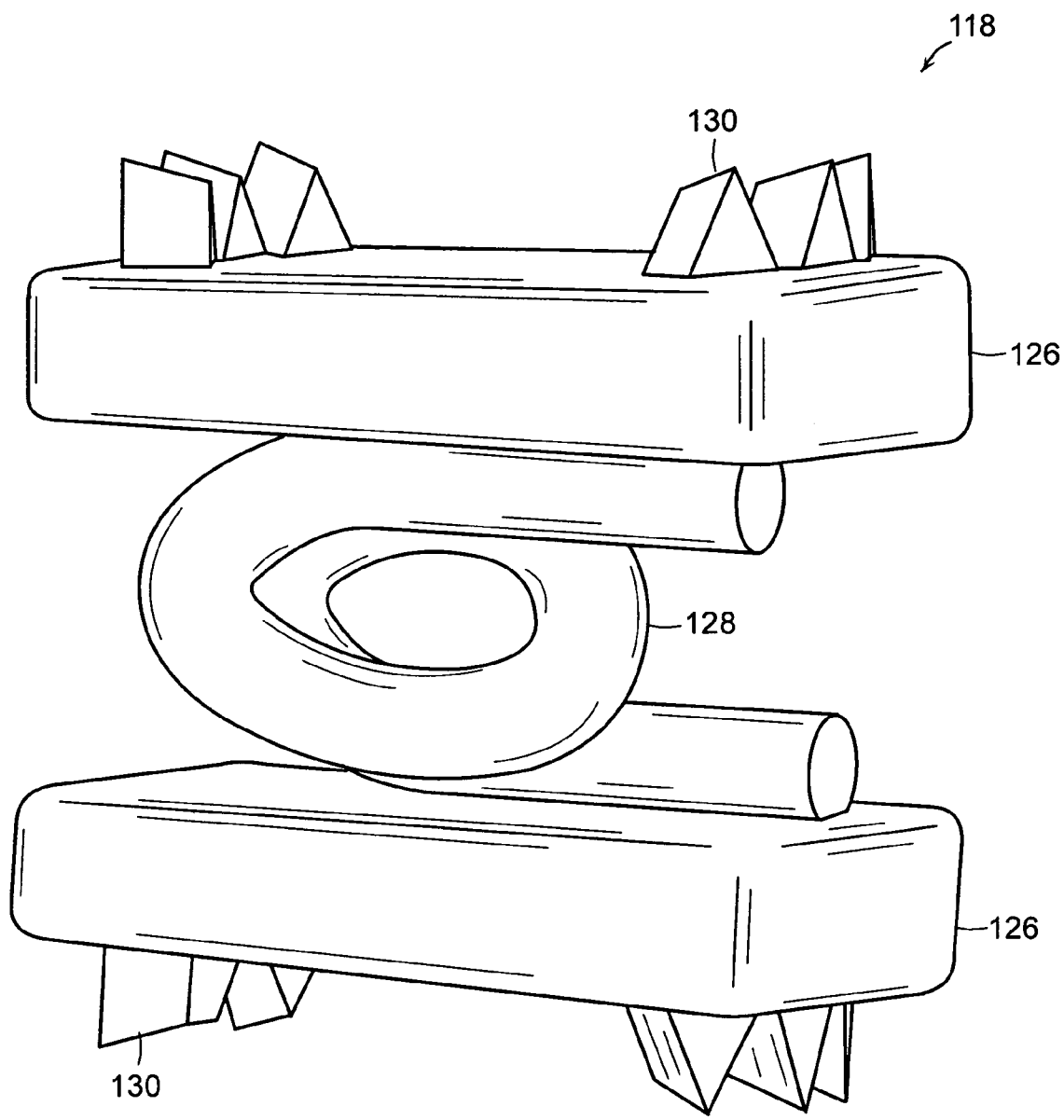
FIG. 13 illustrates an example of a spring element.

FIG. 13 illustrates an example of spring element 118. Spring element 118 can include spring-element plates 126, spring 128, and vertebral bone endplate anchor elements 130.

In one embodiment, the system can include intervertebral prosthetic disc 122 and at least one spring element 118. For example, the system can include an intervertebral prosthetic disc 122 including two plates adapted for insertion between two vertebrae and a core which cooperates with at least one plate at an articular surface; and at least one spring element 118 adapted for insertion between the two vertebrae. In one embodiment, intervertebral prosthetic disc 122 is intervertebral prosthetic disc 82 of FIG. 5. In another embodiment, intervertebral prosthetic disc includes ball and socket components. For example, in one embodiment, a first endplate includes a ball component and a second endplate includes a socket component for receiving the ball component.

Intervertebral prosthetic disc 122 and at least one spring element 118 can be adapted for insertion into an intervertebral space by a posterior or a posterior-lateral surgical approach. For example, intervertebral prosthetic disc 122 can be sized for insertion, e.g., piece-wise insertion of components thereof, into an intervertebral space using a posterior or posterior-lateral approach. In one embodiment, intervertebral prosthetic disc 122 is smaller than a disc used with an anterior surgical operation. Spring elements 118 can thus be used to increase the surface area of the system and to provide additional support to the anatomical structures. Once installed in an intervertebral space, the spring elements 118 can also constrain the motion of vertebral bodies 120 and 124.

Spring elements 118 contact inferior and superior vertebral bodies 120 and 124. Spring elements 118 can include any spring such as, for example, torsion spring 128 or an elastic material. In one embodiment, spring elements 118 include a spring or elastic material sandwiched between two spring-element plates 126 that contact the vertebral bodies 120 and 124. Spring-element plates 126 can include vertebral bone endplate anchor elements 130. In one embodiment, the surfaces of spring-element plates 126 can be textured and/or include an osteoinductive material.

Figure 14:
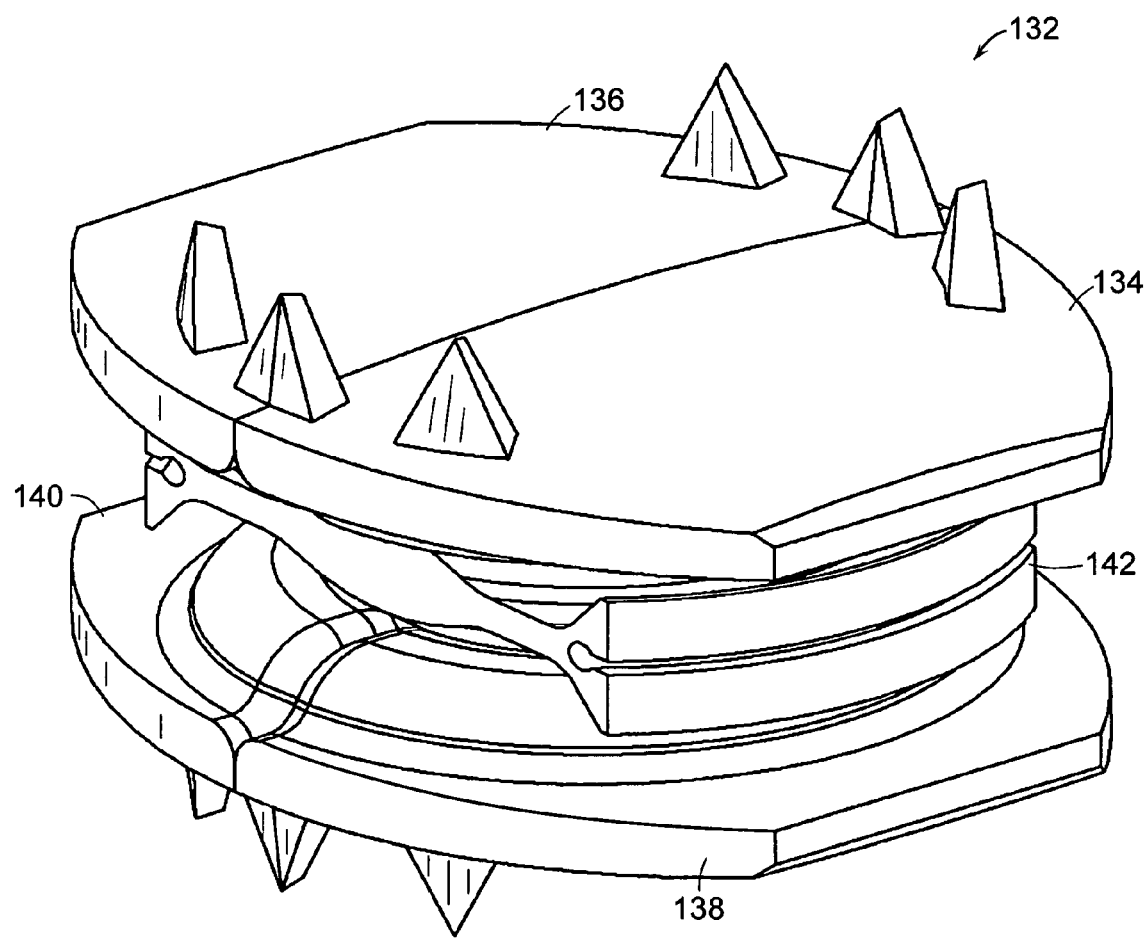
FIG. 14 is a perspective view of an assembled intervertebral prosthetic disc adapted for piece-wise insertion into an intervertebral space using a posterior or posterior-lateral surgical approach.

FIG. 14 is a perspective view of assembled intervertebral prosthetic disc 132 adapted for piece-wise insertion into an intervertebral space using a posterior or posterior-lateral surgical approach. As illustrated, intervertebral prosthetic disc 132 includes a superior endplate assembly having two endplate components 134 and 136 and an inferior endplate assembly having two endplate components 138 and 140. Core 142 includes two core modules 144 and is positioned between the superior and inferior endplate assemblies.

Figure 15:
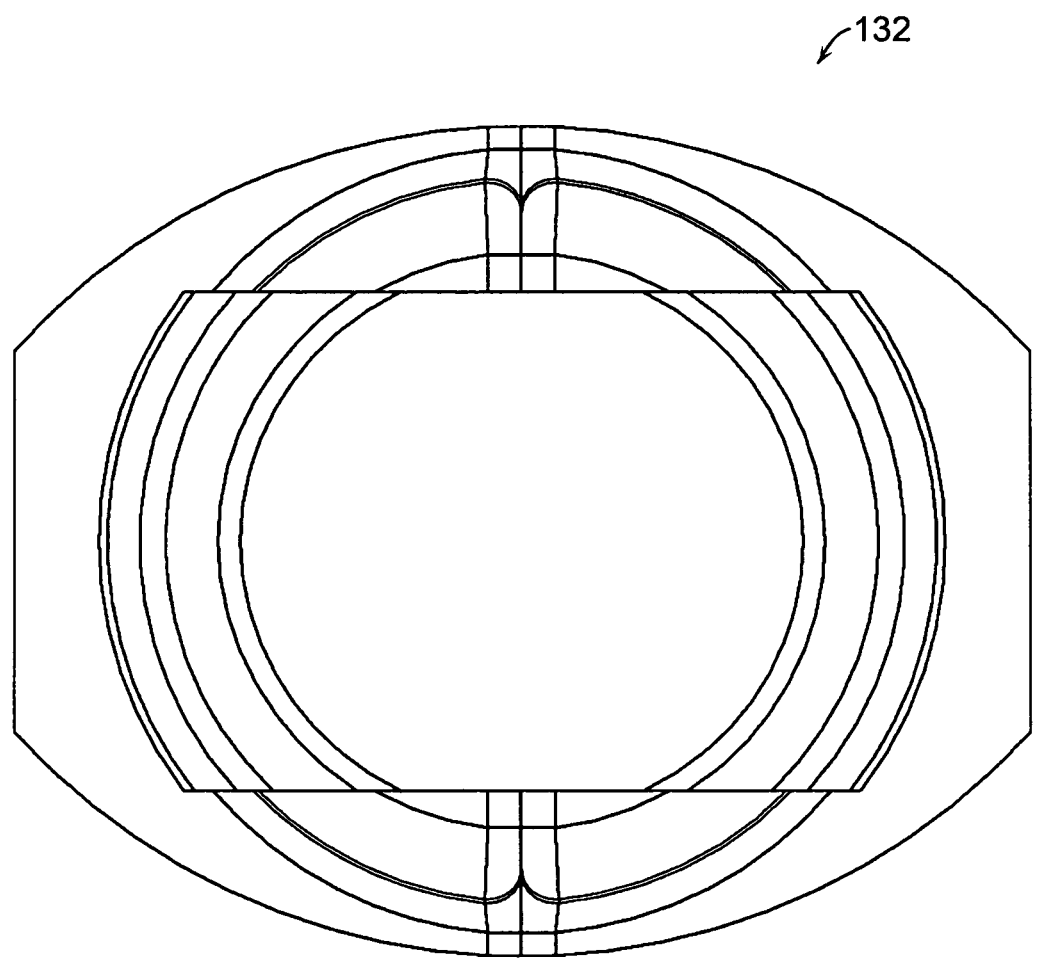
FIG. 15 is a top view of the assembled intervertebral prosthetic disc shown in FIG. 14.

FIG. 15 is a top view of assembled intervertebral prosthetic disc 132 shown in FIG. 14.

Figure 16:
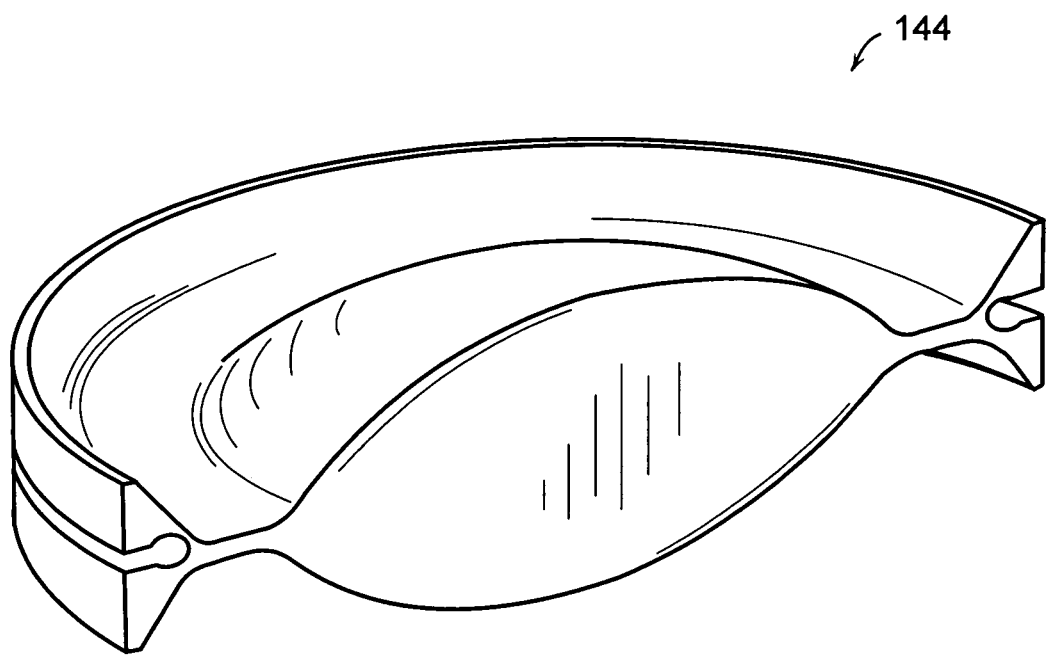
FIG. 16 is a view of a core module of an intervertebral prosthetic disc in one embodiment of the present invention.

FIG. 16 is a view of core module 144 of an intervertebral prosthetic disc. In one embodiment, core module 144 is used in conjunction with endplates which include endplate components 134, 136, 138, and 140.

Figure 17:
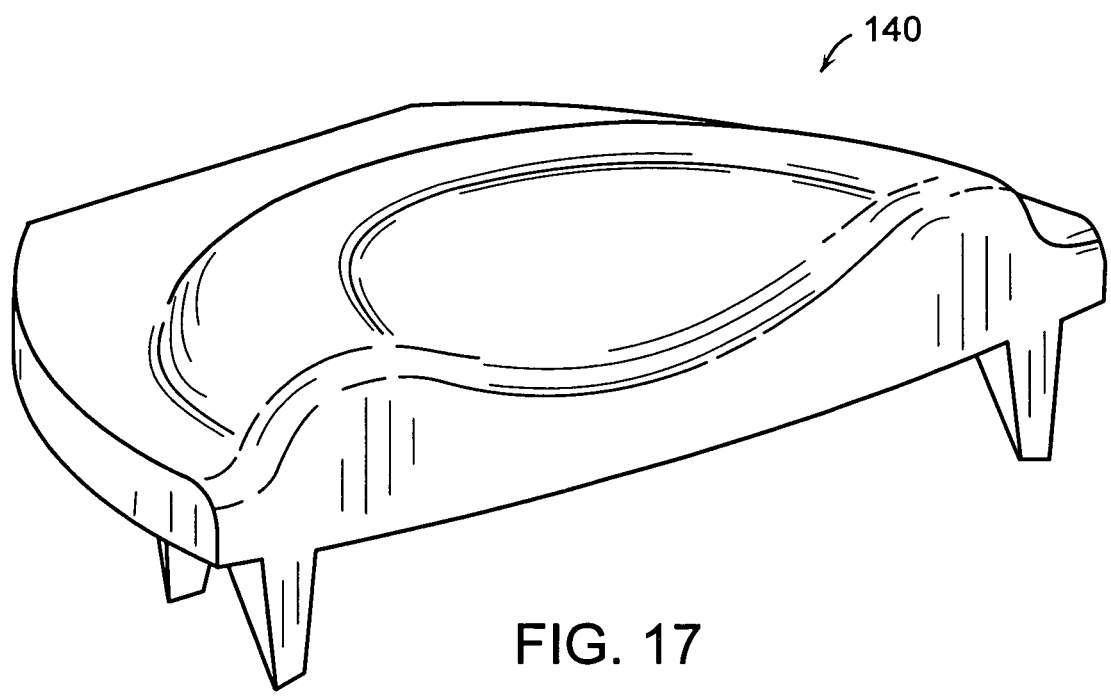
FIG. 17 is a view of an endplate component of an intervertebral prosthetic disc in one embodiment of the present invention.

FIG. 17 is a view of an endplate component, e.g., endplate component 140 of intervertebral prosthetic disc 132 shown in FIG. 14.

In one embodiment of the present invention, intervertebral prosthetic disc 132 includes a superior endplate assembly including a plurality of superior endplate components, e.g., endplate components 134 and 136; an inferior endplate assembly including a plurality of inferior endplate components, e.g., endplate components 138 and 140; and core 142 which includes a plurality of core modules 144 which cooperate with at least one of the superior endplate assembly and the inferior endplate assembly at an articular surface. The superior endplate assembly and the inferior endplate assembly can be adapted for posterior or posterior-lateral insertion between two vertebrae. For example, intervertebral prosthetic disc 132 can be sized for insertion, e.g., piece-wise insertion of components thereof, into an intervertebral space using a posterior or posterior-lateral approach.

In one embodiment, intervertebral prosthetic disc 132 is an intervertebral prosthetic disc designed for insertion into an intervertebral space using an anterior surgical approach wherein the intervertebral prosthetic disc has been sectioned to permit insertion of the components thereof into an intervertebral space using a posterior or posterior-lateral approach. In one embodiment, the superior endplate assembly and/or the inferior endplate assembly includes two endplate components 134 and 136 and/or 138 and 140, respectively. The core 142 can include a plurality, e.g., two, of core modules 144.

In one embodiment, the intervertebral prosthetic disc, e.g., intervertebral prosthetic disc 132, is designed for inline insertion into an intervertebral space. For example, components of the intervertebral prosthetic disc can be inserted into an intervertebral space and rotation of the components is minimized prior to mating and/or seating the components within the intervertebral space. In one embodiment, the intervertebral prosthetic disc, e.g., intervertebral prosthetic disc 132, can be inserted anteriorly at higher levels of the lumbar spine, e.g., above about L4. In one embodiment, components of the intervertebral prosthetic disc are inserted around the great vessels instead of retracting the vessels as could otherwise be necessary. In various embodiments, the core can include a core, for example, as illustrated in FIGS. 7B-7E.

EQUIVALENTS

While this invention has been particularly shown and described with references to preferred embodiments thereof, it will be understood by those skilled in the art that various changes in form and details may be made therein without departing from the scope of the invention encompassed by the appended claims.

We claim:

1. An intervertebral prosthetic disc, comprising:

a) a superior endplate;

b) an inferior endplate; and c) a core including a plurality of core modules slidably disposed between the superior endplate and the inferior endplate so as to allow translation of the superior endplate and the inferior endplate with respect to one another, each of the core modules in a directly abutting relationship with one another, thereby constraining movement of the core modules relative to one another, wherein the superior endplate and the inferior endplate are each configured to receive at least a portion of the core.

2. The intervertebral prosthetic disc of claim 1 wherein at least one of the superior endplate and the inferior endplate defines at least one recess to accommodate the core.

3. The intervertebral prosthetic disc of claim 2 wherein the recess constrains the core from substantial lateral-medial movement relative to the superior endplate and the inferior endplate.

4. The intervertebral prosthetic disc of claim 2 wherein the recess is a truncated cylindrical recess.

5. The intervertebral prosthetic disc of claim 2 wherein the recess is a truncated spherical recess.

6. The intervertebral prosthetic disc of claim 1 wherein the superior endplate includes a first anterior plate and a first posterior plate and wherein either the first anterior plate or the first posterior plate defines a recess to accommodate the core.

7. The intervertebral prosthetic disc of claim 1 wherein the inferior endplate includes a second anterior plate and a second posterior plate and wherein either the second anterior plate or the second posterior plate defines a recess to accommodate the core.

8. The intervertebral prosthetic disc of claim 1 wherein at least one of the superior endplate and the inferior endplate defines a plurality of recesses to accommodate the plurality of core modules.

9. The intervertebral prosthetic disc of claim 8 wherein the superior endplate defines a truncated spherical recess and the inferior endplate defines a plurality of truncated cylindrical recesses.

10. The intervertebral prosthetic disc of claim 8 wherein the inferior endplate defines a truncated spherical recess and the superior endplate defines a plurality of truncated cylindrical recesses.

11. The intervertebral prosthetic disc of claim 1 wherein at least one of the superior endplate and the inferior endplate is adapted to receive a guidewire.

12. The intervertebral prosthetic disc of claim 11 wherein at least one of the superior endplate and the inferior endplate defines a guidewire channel with a generally lateral-medial orientation.

13. The intervertebral prosthetic disc of claim 1 wherein the superior endplate includes a first anterior plate and a first posterior plate.

14. The intervertebral prosthetic disc of claim 13 wherein the first anterior plate and the first posterior plate are adapted for affixation to one another.

15. The intervertebral prosthetic disc of claim 1 wherein the inferior endplate includes a second anterior plate and a second posterior plate.

16. The intervertebral prosthetic disc of claim 15 wherein the second anterior plate and the second posterior plate are adapted for affixation to one another.

17. The intervertebral prosthetic disc of claim 1 suitably sized for placement into an intervertebral space using a posterior or a posterior-lateral surgical approach.

* * * * *